United States Patent [19]

Auerswald et al.

[11] Patent Number: 5,032,573
[45] Date of Patent: Jul. 16, 1991

[54] HOMOLOGS OF APROTININ PRODUCED FROM A RECOMBINANT HOST, PROCESS, EXPRESSION VECTOR AND RECOMBINANT HOST THEREFOR AND PHARMACEUTICAL USE THEREOF

[75] Inventors: Ernst-August Auerswald; Werner Schröder; Eugen Schnabel; Wolfgang Bruns; Gerd Reinhardt, all of Wuppertal, Fed. Rep. of Germany; Michael Kotick, Elkhart, Ind.

[73] Assignee: Bayer Aktiengesellschaft, Leverkusen, Fed. Rep. of Germany

[21] Appl. No.: 416,169

[22] Filed: Oct. 2, 1989

Related U.S. Application Data

[62] Division of Ser. No. 29,501, Mar. 23, 1987.

[51] Int. Cl.$^5$ .............................................. C07K 7/10
[52] U.S. Cl. ...................................... 514/12; 514/21; 530/324
[58] Field of Search .................... 514/12, 21; 530/324

[56] References Cited

U.S. PATENT DOCUMENTS 4,485,100 11/1984 Hochstrasser et al. ............ 424/177
4,595,674 6/1986 Tschesche et al. .................... 514/9

FOREIGN PATENT DOCUMENTS 0132732 2/1985 European Pat. Off. .
0157235 10/1985 European Pat. Off. .
0171024 2/1986 European Pat. Off. .
0207402 1/1987 European Pat. Off. .
86/01229 2/1986 PCT Int'l Appl. .

OTHER PUBLICATIONS

Chemical Abstracts No. 88:185287g of Creighton et al., 1978, J. Mol. Biol., 119(4):507–518.
*The Merck Index*, 10th Edition, 1983, Merck & Co. Inc., Rahway, New Jersey.
Wilcken-Bergmann et al., "A Synthetic Operon Containing 14 Bovon Pancreatic Trypsin Inhibitor Genes is Expressed in E. coli", *EMBO Journal*, vol. 5, #12, pp. 3219–3225 (1986).
Jering et al., "Replacement of Lysin by Arginine, Phenylalanine and Tryptophan in the Reactive Site of the Bovine Trypsin-K Allikrein Inhibitor (Kunitz) and Change of the Inhibitory Properties", *Chemical Abstracts*, vol. 84, p. 29 (1986).
*Journal of Cellular Biochemistry*, Suppl. 9B, 1985, Abstracts of 14th Annual Meetings, Mar. 9–Apr. 4, 1985, Marks, C. B. et al., "Expression and Mutagenesis of Bovine Pancreatic Tyrpsin Inhibitor".
Chem. Abstr., vol. 106 (1987), 62156.
Chem. Abstr. vol., 104 (1986), 1703.
Chem. Abstr., vol. 92 (1980), 142226b.
Chem. Abstr., vol. 89 (1978), 102675.

*Primary Examiner*—Margaret Moskowitz
*Assistant Examiner*—Keith C. Furman
*Attorney, Agent, or Firm*—Sprung Horn Kramer & Woods

[57] ABSTRACT

Microbially produced aprotinin and aprotinin homologs used for treating patients suffering from an excess release of pancreatic elastase, serum elastase or leukocyte elastase.

9 Claims, 13 Drawing Sheets

DNA-Sequence of Oligonucleotides used for construction of synthetic genes consisting of four blocks (alpha, beta, gamma, delta)

| | | |
|---|---|---|
| Fra | 1 | AATTCATGCGTCCGGACTTCTGCCTCGAGC |
| Fra | 2 | CAGAAGTCCGGACGCATG |
| Fra | 3 | CGCCGTACACTGGGCCCTGCAAAGCT |
| Fra | 4 | CCCAGTGTACGGCGGCTCGAGG |
| Fra | 5 | CGTATCATCCGTTACTTC |
| Fra | 6 | ATGATACGAGCTTTGCAGGG |
| Fra | 7 | TACAATGCAAAGGCAGGCCTGTGTCAGACC |
| Fra | 8 | CCTGCCTTTGCATTGTAGAAGTAACGG |
| Fra | 9 | TTCGTATACGGCGGTTGCCGTGCTAAGCGT |
| Fra | 10 | AACCGCCGTATACGAAGGTCTGACACAGG |
| Fra | 11 | AACAACTTCAAATCCGCGGAAGACTGCGAA |
| Fra | 12 | ATTTGAAGTTGTTACGCTTAGCACGGC |
| Fra | 13 | CGTACTTGCGGTGGTGCTTAGTAAAGCTTG |
| Fra | 14 | CACCGCAAGTACGTTCGCAGTCTTCCGCGG |
| Fra | 16 | GATCCAAGCTTTACTAAGCAC |

FIG. 2a

Sequence of the Beta-EA2-Block
(Leu-15 modification, CTG)
sites: ApaI StuI

```
    CTGCCTGGCTCGTATCATCCGTTACTTCTACAATGCAAAGGCAGG
 1  ---------+---------+---------+---------+-----  45
    GACGGACCGAGCATAGTAGGCAATGAAGATGTTACGTTTCCGTCC

CysLeuAlaArgIleIleArgTyrPheTyrAsnAlaLysAla???
```

Sequence of the Beta-EA4-Block
(Val-15 modification, GTT)
sites: ApaI-StuI

```
    CTGCGTTGCTCGTATCATCCGTTACTTCTACAATGCAAAGGCAGG
 1  ---------+---------+---------+---------+-----  45
    GACGCAACGAGCATAGTAGGCAATGAAGATGTTACGTTTCCGTCC

CysValAlaArgIleIleArgTyrPheTyrAsnAlaLysAla???
```

Sequence of the Beta-EA5-Block
(Ile-15 modification, ATC)
sites: ApaI-StuI

```
    CTGCATCGCTCGTATCATCCGTTACTTCTACAATGCAAAGGCAGG
 1  ---------+---------+---------+---------+-----  45
    GACGTAGCGAGCATAGTAGGCAATGAAGATGTTACGTTTCCGTCC

CysIleAlaArgIleIleArgTyrPheTyrAsnAlaLysAla???
```

FIG. 2b

DNA-Sequence of the synthetic Glu-52-Aprotinin Gene
(EcoR1-BamH1, partial-Sequence of pRK 63.1.1)

```
                E                                              A
                C                                              P
                O                                              A
                R                                              I
                I
      AATTCATGCGTCCGGACTTCTGCCTCGAGCCGCCGTACACTGGGCCCTGCAAAGCTCGTA
  1   ---------+---------+---------+---------+---------+---------+  60
      TTAAGTACGCAGGCCTGAAGACGGAGCTCGGCGGCATGTGACCCGGGACGTTTCGAGCAT c:            ArgProAspPheCysLeuGluProProTyrThrGlyProCysLysAlaArgIle
```

```
                              S
                              T
                              U
                              1
      TCATCCGTTACTTCTACAATGCAAAGGCAGGCCTGTGTCAGACCTTCGTATACGGCGGTT
 61   ---------+---------+---------+---------+---------+---------+  120
      AGTAGGCAATGAAGATGTTACGTTTCCGTCCGGACACAGTCTGGAAGCATATGCCGCCAA c:        IleArgTyrPheTyrAsnAlaLysAlaGlyLeuCysGlnThrPheValTyrGlyGlyCys
```

```
                                       S
                                       A
                                       C
                                       2
      GCCGTGCTAAGCGTAACAACTTCAAATCCGCGGAAGACTGCGAACGTACTTGCGGTGGTC
121   ---------+---------+---------+---------+---------+---------+  180
      CGGCACGATTCGCATTGTTGAAGTTTAGGCGCCTTCTGACGCTTGCATGAACGCCACCAC

ArgAlaLysArgAsnAsnPheLysSerAlaGluAspCysGluArgThrCysGlyGlyAla
```

```
              H
              I       B
              N       A
              D       M
              3       HI
      CTTAGTAAAGCTTG
181   ---------+----  194
      GAATCATTTCGAAC
```

FIG. 3

Aprotinin  40 42 43 44 45 46 47 48  fraction

FIG.11
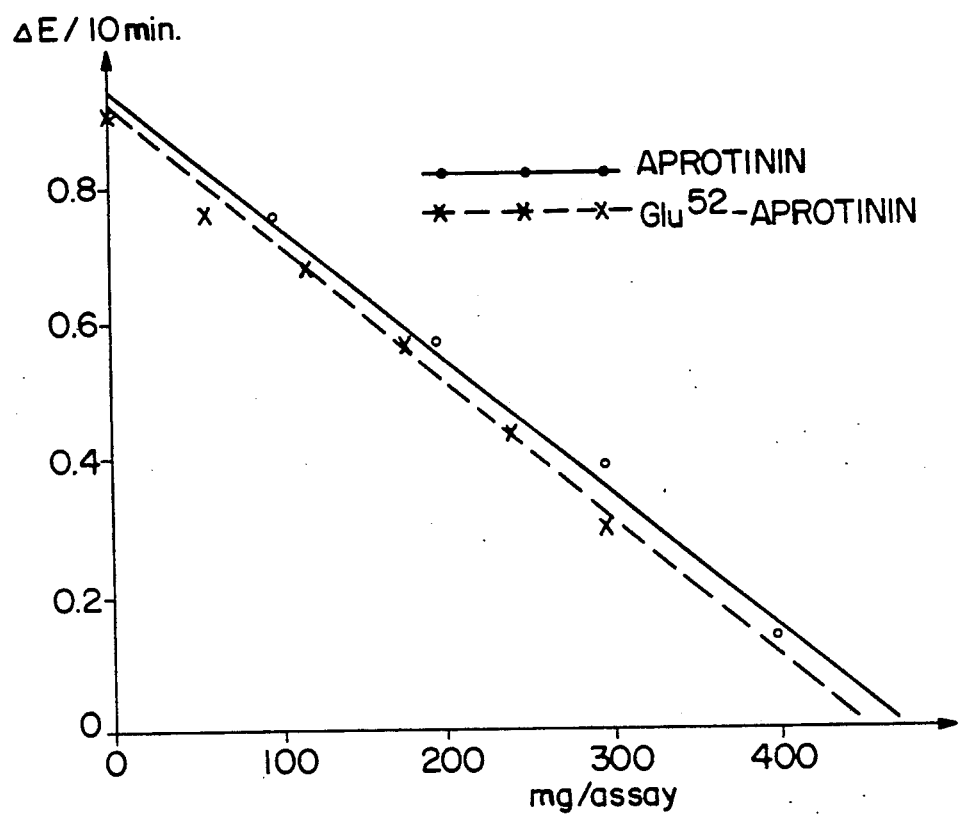
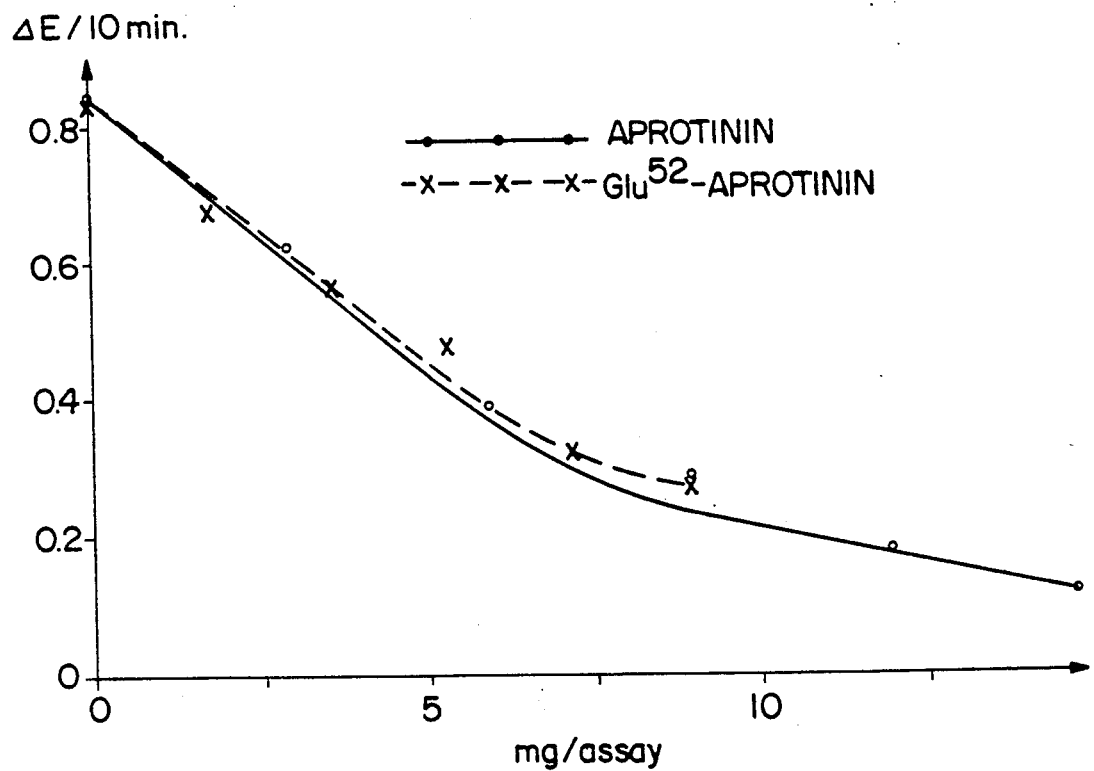

5,032,573

HOMOLOGS OF APROTININ PRODUCED FROM A RECOMBINANT HOST, PROCESS, EXPRESSION VECTOR AND RECOMBINANT HOST THEREFOR AND PHARMACEUTICAL USE THEREOF

This is a division of application Ser. No. 07/029,501, filed 3/23/87, now pending.

BACKGROUND OF THE INVENTION

1. Field of the Invention

This invention relates to aprotinin homologs and their production via recombinant DNA technology.

The chemically synthesized DNA molecules as disclosed herein are characterized by the DNA sequence coding for new polypeptides or polypeptides substantially agreeing in the amino acid sequence and composition of aprotinin or aprotinin homologs and having the biological activity of aprotinin or of aprotinin homologs.

2. Background Information

Aprotinin is a well known peptide comprising 58 amino acids and having the ability to inhibit trypsin, chymotrypsin, plasmin and kallikrein. Aprotinin is a basic proteinase inhibitor derived from bovine organs and has become a valuable drug, named Trasylol ®, for the treatment of various diseases like, e.g., hyperfibrinolytic hemmorrhage and traumatic-hemorrhagic shock (see H. Fritz and G. Wunderer, (1983), *Drug Res.*, 33, 479–494).

Recently it has been shown, that homologs of aprotinin with other aminoacids in position 15, instead of lysine, are valuable proteinase inhibitors having modified effects and efficacies in comparison to aprotinin (DE-OS No. 33 39 693; H. R. Wenzel et al, 1985, in *Chemistry of Peptides and Proteins*, Vol. 3). These aprotinin homologs have strong inhibitory effects on the elastases from pancreas and leukocytes, and on cathepsin G.

Such homologs of aprotinin can be used therapeutically in diseases in connection with excessive release of pancreatic elastase (pancreatitis), serum elastase (artherosclerosis), leukocyte elastase in acute and chronic inflammations with damage to connective tissue, in damage to vessel walls, in necrotic diseases and degeneration of lung tissue. Equally important is the part played by lysosomal enzymes, in particular leukocyte elastase, in inflammatory reactions due to immunological processes, for example, rheumatoid arthritis.

Although aprotinin and aprotinin homologs can be obtained from bovine organs and by semisynthetic conversion of the bovine trypsin inhibitor (Tschesche, M., Wenzel, M., Schmuck, R., Schnabel, E., Offenlegungsschrift DE No. 33 39 693), the yields are relatively small.

It was perceived that the application of recombinant DNA and associated technologies would be the effective way of providing the necessary large quantities of high quality aprotinin homologs. The goal was to produce aprotinin homologs biologically active, as products of recombinant DNA technology from a host organism.

Methods for the expression of heterologous DNA in a microorganism are now known.

DNA coding for polypeptides of known amino acid sequences may be prepared by using the genomic DNA sequence, the cDNA sequence which is complementary to the mRNA or by choosing codons according to the genetic code and preparation of a synthetic gene.

A partial DNA sequence of a bovine genomic clone from bovine pancreatic trypsin inhibitor gene was cloned by S. Anderson and I. B. Kingston, (1983), *Proc. Natl. Acad. Sci. USA*, 80, 6838–6842 to characterize a genomic clone for BPTI.

A larger segment of the bovine genome coding for BPTI and bovine spleen inhibitor II were recently sequenced and published by Kingston, I. B. and Anderson, S., (1986), *Biochem. J.*, 233, 443–450.

SUMMARY OF THE INVENTION

It is object of the present invention to provide aprotinin homologs, nucleic acids encoding them, vectors incorporating the nucleic acids and cells transformed therewith and methods of obtaining aprotinin homologues.

For the present purpose it was most advantagous to choose codons for preparing synthetic genes with a proper design and which promise widespread application.

This is especially the case by constructing a synthetic master gene comprising DNA blocks or cassettes terminated by unique recognition sites of restriction enzymes. Such a gene design allows easy modification or mutation of all DNA sequences within such DNA blocks.

Homologs of aprotinin were prepared by recombinant DNA technology. Such homologs of aprotinin, for example, Val-15-, Ile-15-, Leu-15-, Phe-15- and Ala-15-, Arg-15, Gly-15, Ser-15, Trp-15, Tyr-15, aprotinin alone or in combination with a substitution at position 52 by Glu, Leu, Val, Arg or Thr have been found to be equivalent to the known aprotinin and its homologs, which have Met at position 52 and are disclosed together with their production. The substitution of Met-52 allows production of aprotinin and aprotinin homologs in which a genetically engineered fused polypeptide is cleaved by cyanogen bromide at Met in the fused polypeptides.

The synthetic DNA coding for such homologs, recombinant plasmids comprising structural genes for expressing the homologs and *E. coli* transformed by the recombinant plasmids are also disclosed.

BRIEF DESCRIPTION OF THE DRAWINGS

FIG. 2a depicts DNA sequences for sixteen DNA fragments used for producing synthetic aprotinin.

FIG. 2b depicts DNA sequences for three beta-blocks.

FIG. 3 depicts a DNA sequence of a master gene used for producing synthetic aprotinin.

FIG. 11 are two graphs (dose curres) depicting a comparison of aprotinin and Glu-52-aprotinin by trypsin inhibitory activity.

DETAILED DESCRIPTION OF THE INVENTION

In the following, the strategy for construction and selection of DNA fragments coding for aprotinin and aprotinin homologs is shown.

The known protein sequence and the genetic code of aprotinin and aprotinin homologs were used to determine a DNA sequence coding for such polypeptides.

The degeneracy of the genetic code permits substantial freedom in the choice of codons for any given amino acid sequence.

All possible base substitutions among the codons designating the amino acid sequence of this protein were determined. According to this, all potential restriction sites located within the possible DNA sequences were determined.

The codon choice for master genes were guided by the following considerations:

First, codons and fragments were selected, and fragment assembly was designed, so as to avoid undue complementarity of the fragments.

Secondly, regions rich in A-T base pairing are avoided to overcome problems with premature termination of transcription.

Thirdly, restriction sites were chosen necessary for facilitating verification of transformants or base substitutions by replacement of appropriate fragments with other fragments so that one can produce easily modifications of aprotinin, examine the relationship between the structures and their activities.

Fourthly, a majority of the codons chosen are those preferred in the expression of microbial genomes (see H. Grosjean and W. Fiers, *Gene,* 18 (1982), 192-209; M. Gouy and C. Gautier, *Nucleic Acids Research,* 10, (1982), 7055-7074).

Figure 1:
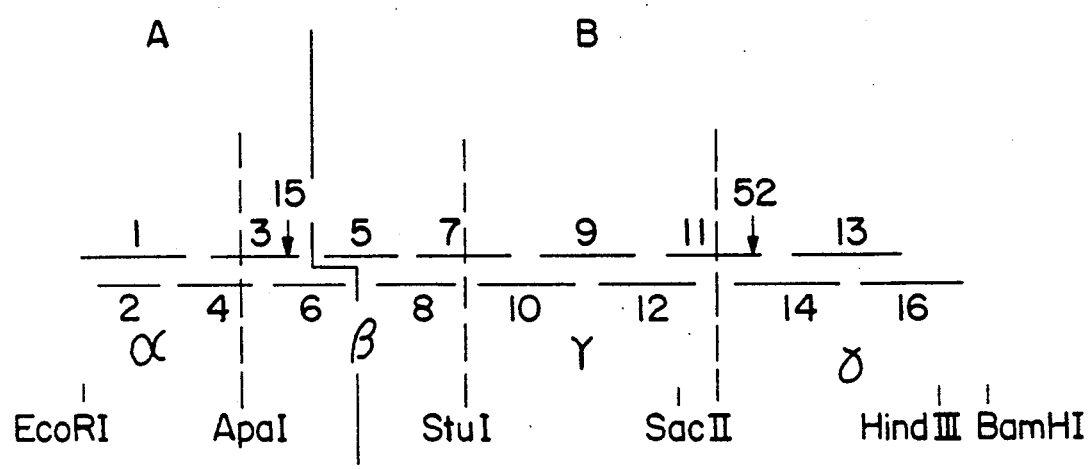
FIG. 1 is a schematic diagram indicating a design of a synthetic aprotinin gene.

The principal design for synthetic aprotinin genes and their homologs is shown in FIG. 1.

The design of the synthetic master gene, consisting of four blocks (named α, β, γ, δ) surrounded by recognition sites for restriction endonucleases, further allows easy modifications and alterations of DNA sequences (codon usage, mutations, protein engineering, (amplification of the genes) for unfused and fused expressions.

The synthetic genes were constructed as follows:

The synthetic genes for aprotinin and aprotinin homologs were constructed via a master gene by the assembly of 15 purified oligonucleotides which have overlapping terminal regions (see FIG. 1). This construction was done in two steps. First, part A and part B of the gene were produced by hybridization, ligation and purification of DNA fragments 1, 2, 3, 4 and 6 for part A and DNA fragments 5, 7, 8, 9, 10, 11, 12, 13, 14 and 16 for part B (FIG. 2). Second, part A and B of the gene were ligated and purified. For this construction we used materials and methods which are described hereafter. The DNA sequence of the master gene is shown in FIG. 3. It includes the initiation codon ATG, two termination codons, TAG and TAA, the 5' terminal restriction site for Eco RI and the 3' terminal restriction sites for Hind III and Bam HI, and also the internal restriction sites for Apa I, Stu I, Sac II (Sst II). These sites especially the internal ones, facilitate the cloning of the coding sequence, the modification of the master gene by exchanging DNA fragments which codes for other amino acids or which have another codon usage. An amplification of the gene can be done easily by adding appropriate linker sequences. The total spectra of protein engineering is possible with such a construction.

To construct genes for aprotinin homologues only a restriction fragment with the appropriate DNA sequence has to be exchanged. Sequences for such fragments which will code for amino acid alterations including positions 15 and 52 were given in FIG. 2b.

The recombinant plasmids were constructed as follows:

The plasmid chosen for experimental aprotinin cloning was pUC 8 (J. Vieira and J. Messing, (1982), *Gene,* 19, 259). This cloning vector consists of a pBR 322 derived ampicillinase gene and the origin of DNA replication ligated to a portion of the lac Z gene which contains an array of unique restriction enzyme recognition sites. When this vector is introduced into lac *E. coli,* the transformants give rise to blue colonies on appropriate indicator plates. Cloning DNA fragments into any of the multiple restriction sites, for example between Eco RI and Bam HI, inactivates the lac gene giving rise to white colonies. Plasmid pUC 8 is commercially available from P-L Biochemicals (see below).

The expression plasmids were constructed as follows:

For expression of aprotinin and aprotinin homologs as a fusion protein a plasmid has been constructed in which the appropriate gene was fused with the carboxy terminus of the β galactosidase gene as it was shown in similar experiments by U. Rüther and B. Müller-Hill, (1983), *EMBO Journal,* 2, p. 1791-1794. The parental plasmid pUR 278 has the single cloning sites, Bam HI, Sal I, Pst I, Xba I and Hind III at the 3' end of the lac Z gene (see also German patent application No. P 3 309 501.9). Insertion of a coding DNA sequence in the proper cloning sites and in the correct reading frame leads to a fusion protein of active β galactosidase combined with the peptide encoded by the DNA.

Figure 6:
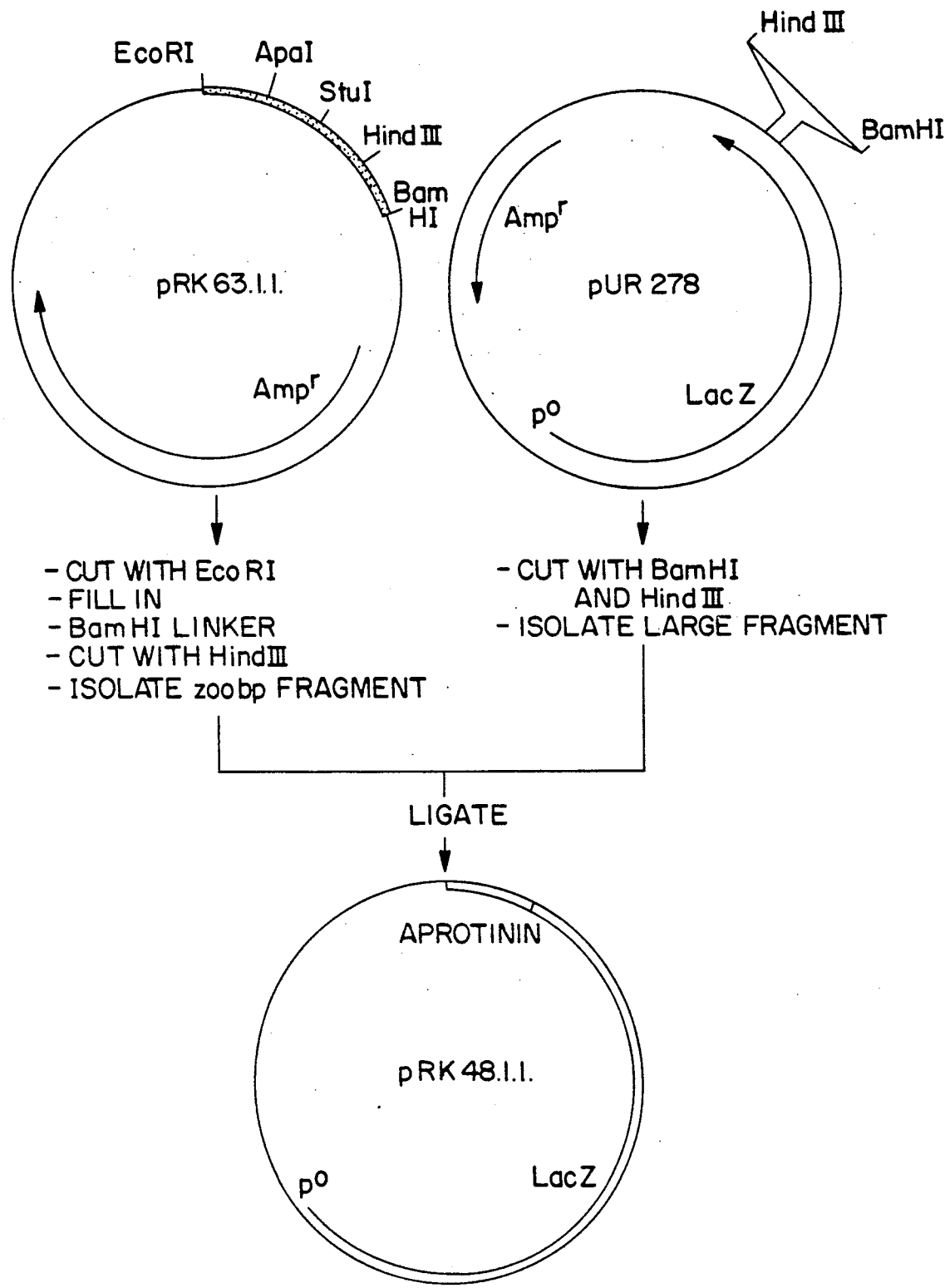
FIG. 6 schematically depicts the construction of a plasmid according to the present invention.

The restriction sites Bam HI and Hind III of expression vector pUR 278 were chosen for cloning the synthetic genes for aprotinin and aprotinin homologues in an expression vector. Therefore, it was necessary to modify the aprotinin gene by adding a Bam HI site at the 5' Eco RI end of the gene and using the Hind III site at the 3' end (see also FIG. 6).

The following standard material and methods for recombinant DNA work were used:

The herein described synthetic genes, recombinant plasmids and expression vectors with such genes can be prepared and characterized by the following material and methods.

Material

Enzymes

Polynucleotid-Kinase (PNK), 5,5 units/μl No. 633 542; Boehringer-Mannheim GmbH Biochemica, P.O. Box 310120, D-6800 Manheim 31, FRG DNA Polymerase; Klenow, Boehringer-Mannheim No. 104 523 T4 DNA ligase, 0.9 units/μl; Boehringer-Mannheim No. 481 220

Restriction enzymes were purchased from Bethesda Research Laboratorie GmbH, Offenbacher Str. 113, D-6078 Neu-Isenburg 1, FRG; Boehringer-Mannheim, Biolabs, 32 Tozer Road, Beverly, Mass. 01915-9990 U.S.A.

Calf intestinal alkaline phosphatase (CIP); Boehringer-Mannheim

Lysozyme; RNase A; Boehringer-Mannheim

Reagents

Gamma 32 P ATP; Amersham No. PB 10168
Alpha 32 P-dTTP; Amersham 167
ATP; Sigma No. A-6144; Sigma Chemie GmbH, Grünwalden Weg 30, D-8024 Deisenhofen, FRG
Bis Acrylamide; Serva 29195; Feinbiochemica GmbH & Co., D-6900 Heidelberg 1, Postfach 105260
Acrylamide; Serva and Bio-Rad 161-0103; Bio-Rad Laboratories GmbH, Dachauer Str. 364+511 P.O. Box 50-0167, D-8000 München 50, FRG
TEMED; Serva 35925
Ammonium Persulfate; Serva 13375
Urea; BRL ultra pure 5505 UA
DE 52 (preswollen diethylaminoethyl cellulose); Whatman, Cat 4075-050 W. & R. Balston Ltd, Springfield Mill, Mardstone, Kent, GB
DTE; Serva 20697
Isopropyl-$\beta$-D-thiogalactoside (IPTG); Sigma I 5502
5-brom-4-chlor-indolyl-$\beta$-D-galactoside (X gal); Boehringer-Mannheim 651745
N,N'-dimethylformamid; Merck 2 203 034: E. Merck, Frankfurter Str. 250 D-6100 Darmstadt 1, FRG
EGTA
Saccharose; BRL 5503 UA
Diaminopimelin acid; Sigma D 1377
M 13-Dideoxynucleotide Sequencing System; New England Biolabs, Beverly, Mass., U.S.A. #408, #409
chloroform
 isoamylalcohol
Thymidine; Serva 18600
Glucose D (+); Merck 8337
Tris; Merck 8382
Kaliumhydroxid; Merck 5033
Calciumchlorid; Merck 2382
Rubidiumchlorid; Sigma R 2252
Manganchlorid; Sigma M 3634
DMSO; Sigma D 5879
EDTA;
Potassium acetate;
SDS;

DNA

Plasmid pUC 8; 27-4916-xx Bam HI linker; Pharmacia P-L Biochemicals, Munzinger Str. 9, Postfach 5480, D-7800 Freiburg 1, FRG

Media and Antibiotics

Bacto-tryptone; Difco 0123-01
Bacto-yeast-extract; Difco 0127-01
Bacto-Agar; 0140-01
LB-Medium: (for 1 ltr) 10 g Bacto-Trypton, 5 g Bacto-yeast-extract, 10 g NaCl, adjust pH 7.5 with NaOH)
kappa 1776-Medium: (for 1 liter) 25 g Bacto-Trypton, 7.5 g Bacto-yeast-extract, 1M Tris-HCl (pH 7.5) 20 ml, ad 950 ml, autoclave and cool down, add sterile: 5 ml 1M MgCl 2, 10 ml 1% diaminopimeline acid, 10 ml 0.4% thymidine, 25 ml 20% glucose
YT-Medium: (for 1 liter) 8 g Bacto-Trypton, 5 g Bacto-yeast-extract, 5 g NaCl
Agar plates were prepared by adding 15 g Bacto-Agar to 1 ltr of the appropriate medium.

Indicator plates: To 1 liter autoclaved YT medium with 1.5% agar the following solutions were added: 2 ml 0.1M IPTG, 2 ml of 2% X-gal in N,N' dimethylformamide and 2 ml 100 mg/ml ampicillin.

Antibiotics
Chloramphenicol; Boehringer Mannheim 634 433
Ampicillin; Serva 13397
Tetracycline; Serva 35865

Buffers and Solutions

20 $\mu$M ATP: in water
10 mM ATP: in water
10X PNK-Mix: 0.5M Tris-HCl (pH 7.6); 0.1M MgCl 2; 50 mM DTE; 1 mM EDTA
10X Ligase-Mix: 0.5M Tris-HCl (pH 7.4); 0.1M MgCl 2; 0.1M DTE; 10 mM ATP
10X SP-50: 100 mM Tris-HCl (pH 7.5); 100 mM MgCl 2; 500 mM NaCl; 10 mM DTT
10X SP-100: 100 mM Tris-HCl (pH 7.5); 100 mM MgCl 2; 1M NaCl; 10 mM DTT
10X SP-0: 100 mM Tris-HCl (pH 7.5); 100 mM MgCl 2; 10 mM DTT
1M TBE: 1M Tris; 0.83M Boric acid; 10 mM EDTA; pH 8.3
3X Formamide Dye Mix: 70% formamide; 20% glycerol; 1 mM EDTA; 0.33 mg/ml bromphenol blue; 0.66 mg/ml xylenecyanol FE; 0.66 mg/ml orange G
20X E-buffer: 0.8M Tris; 0.4M sodium acetate; 40 mM EDTA; pH 8.3
10X CIP-buffer: 0.5M Tris-HCl (pH 9.0), 10 mM MgCl 2, 1 mM ZnCl 2, 10 mM Spermidine
Transformation buffer: Prepared as follows, 15 g saccharose, 1 ml 3.5M KOH, 1 ml 1M CaCl 2, 2 ml 5.0 m RbCl bring to 50 ml with aqua bidest, adjust pH 6.2 with 10% acetic acid, add 1 ml 4.5M MnCl 2, adjust pH 5.8 with 10% acetic acid, fill to 100 ml with Aqua bidest and filter sterile.
TE buffer: 10 mM Tris-HCl ph 8.0, 0.1 mM EDTA
10X NT-buffer:
Lysozyme mix: 50 mM glucose, 1 mM EDTA, 10 mM Tris-HCL ph 8.0
Phenol/Sevag: mixture of 1 volume 80% phenol and 1 volume Sevag (Chloroform: iso amylalcohol 24:1)

Standard Methods

Standard Methods for recombinant DNA work were used as described in Maniatis et al, (1982), *Molecular Cloning*, Cold Spring Harbor Laboratory, Cold Spring Harbor, U.S.A. with some modifications as described hereinafter.

Standard Ethanol Precipitation

DNA pellets were dissolved or solutions were adjusted to 0.3M sodium acetate, two volume parts of ethanol were added, incubated at −70° C. for 15 minutes and centrifuged. Pellets were washed twice with 80% ethanol and dried under vacuum.

Standard Phenol Extraction

Solutions were mixed thoroughly with phenol/sevag, volume ratio 1:1, centrifuged, the phenol phase was reextracted with 1/10 volume of buffer or water, the aqueous phases were pooled.

Standard Isolation of DNA Fragments after Polyacrylamide Gel Electrophoresis Small DNA fragments (up to 250 nucleotides) were separated by gel electrophoresis and bands were made visible by autoradiography or UV light (pre-coated TLC-plates Silgur-25, Macherey-Nagel GmbH & Co. KG, Postfach 307, D-5160 Düren). Bands were sliced out, mashed with a siliconized glass rod, eluted with about 400 μl TE buffer pH 8.0 at 42° C. for 18 hours. The material was centrifuged and the pellet reeluted at 42° C. for 4 hours and centrifuged. Both supernatants were combined and purified by anion-exchange-chromatography on small DE-52 pasteur pipette columns with 1M TEABC buffer. After lyophilization DNA was dissolved and lyophilized in water twice.

Standard Ligation

For standard ligation (fragment smaller than vector) a molar ratio of 1:5 were used for vector:fragment. Final DNA concentration was 25 μg/ml. DNA was solved in a small amount of TE buffer, 10X-Ligase mix, T4 DNA ligase were added, adjusted to 1X Ligase mix concentration (50 mM Tris-HCl pH 7.4, 10 mM MgCl 2, 10 mM DTE, 1 mM ATP; standard volume 30 ul). Reaction was performed at 14° C. for 16 hours.

Standard 5' Labelling of DNA Fragments

Dephosphorylated DNA (final concentration about 0.2 μM) was solved in 1X Kinase buffer I (50 mM Tris-HCl pH 7.6, 10 mM MgCl 2, 5 mM DTE, 0.1 mM EDTA). Together with unlabelled ATP, gamma 32 P ATP (3000 Ci/mmol) was added. Final concentration of ATP was always larger than 1 μM. Reaction was carried out with an 500-1000 fold excess of polynucleotid kinase calculated on the unit definition and the DNA concentration, at 37° C. for 30 minutes. Reaction was stopped for phenol extraction. DNA was precipitated with ethanol, washed and dried.

Standard Restriction Endonuclease Digestion

Restriction endonuclease digestions were carried out mainly according to the manuals of the producers. Purified salt free DNA was dissolved in buffer (SP-0, SP-50 or SP-100 respectively to the enzyme used) and digested with an appropriate amount of enzyme. Finally material was phenol extracted and ethanol precipitated.

Standard Isolation of DNA Fragments after Agarose Gel Electrophoresis

DNA fragments were separated by agarose gel electrophoresis (see T. Maniatis et al, (1982), Cold Spring Harbor Laboratory, *Molecular Cloning*) stained with ethidium bromide and cut out under long wave UV light. Slices were put into a dialysis bag, filled with 0.5X E-buffer (volume ratio, buffer:gel slice as 1.5:1) and must be well surrounded by buffer. The sealed bag, air bubble free, was placed into an electrophoresis chamber filled with 0.5X E-buffer. Electrophoresis was carried out for 30 minutes at 200 V, than polarity of the current was reversed for 30 seconds to release the DNA from the wall of the dialysis bag. The buffer surrounding the gel slice was carefully removed and purified further on DEAE cellulose or DE 52 columns (see above).

Standard Dephosphorylation of DNA

DNA completely digested and purified was dissolved in water and adjusted to 1X CIP-buffer (standard total volume 48 μl). Reaction was started at 37° C. by addition of 1 μl (20 units) calf intestine phosphatase (CIP) after 30 minutes again 1 μl CIP was added. Reaction was stopped after 1 hour by adding 5 μl of 50 mM EGTA and incubation at 65° C. for 10 minutes. For dephosphorylation of DNA with blunt ends or recessed 5' termini, repeated incubations were done for 15 minutes at 37° C. and for 15 min at 56° C., respectively. The DNA was extracted with phenol/sevag and precipitated with ethanol.

Autoradiography

Films: AGFA-Gevaert, Curix RP 1, 100 AFW, Kodak XAR 5, 165 1512 x-ray developer; AGFA G153, Kodak LX24 x-ray fixer; AGFA G353; Kodak AL4.

Standard Transformation Procedure

Transformations were done, using the procedure of D. Hanahan ((1983), *J. Mol. Biol.*, 166, 557-580).

1 ml of a 20 ml overnight culture of the host strain inoculated with a single colony and grown in kappa 1776 medium (37° C., shaker with 200 μpm), was used to inoculate 100 ml of prewarmed (37° C.) kappa 1776 medium.

This culture was cultivated under the same conditions. Cell growth was stopped at 0.2 OD 500 nm. After cooling to 4° C. and centrifugation, cell pellet was well resuspended in 20 ml ice cold transformation buffer and incubated at 0° C. for 5 minutes. The suspension was centrifuged again (3000 rpm, 4° C., 15 minutes) and resuspended in 4 ml ice cold transformation buffer. After adding 7 μl DMSO to 200 μl aliquots cells were incubated further at ice water for 15 minutes to 60 minutes. To such an aliquot of competent cells, DNA solved in 20 μl TE was added and the mixture incubated in ice water 20 minutes and at 42° C. for 3 minutes 1 ml of preheated (37° C.) kappa 1776 medium was inoculated by such an aliquot and a cultivation at 37° C. for 1 hour was carried out. For plating the transformants, cells were spun down (3000 rpm, 15 minutes, 4° C.), resuspended in YT medium and plated on indicator plates. According to the expected number of transformants a certain amount of the suspension was used for plating.

Standard Rapid Analytical Plasmid Isolation

This procedure is a modification of the method from Birnboim and Doly, 1979 Nucl. Acids Res. 7, 1513, (see also T. Maniatis et al, 1982). From each transformant which should be analysed a 2 ml overnight culture is prepared (wooden tooth pick, 37° C., 16 hours, rotating wheel). 1.5 ml of the overnight culture was centrifuged for 1 minute at 12,000 g (Eppendorf centrifuge). Pellet was redissolved in a freshly prepared solution of 2 mg lysozyme per ml lysozyme mix and than incubated at 20° C. for 5 minutes. The sample was incubated for 5 minutes on ice after addition of freshly prepared ice cold 0.2M NaOH which contains 1% SDS. For precipitation of chromosomal DNA and proteins 150 μl ice cold potassium acetate pH 4.8 was added. After incubation for 5 minutes at 0° C. and centrifuged for 10 minutes with 12,000 g the plasmid containing supernatant was transferred to a fresh tube and extracted with chloroform/isoamylalcohol (24:1). 500 μl isopropanol were added to the aqueous phase. Mixture was incubated at −20° C. for 30 minutes. After centrifugation (10 minutes, 12,000 g) sediment was washed with 80% ethanol and dried briefly in a vacuum. This material is sufficient for 5 to 6 different restriction analysis by gel electrophoresis.

Standard Purification of Oligonucleotides with Polyacrylamide Gel Electrophoresis Oligonucleotides (about 20 OD 260 nm) were dissolved in buffered formamide (0.1M TBE) and separated electrophoretically on 7M urea, 20% polyacrylamide gels (Maxam and Gilbert, *Meth. Enzymol.*, 65, 500–560, (1980)). Gels were put on fluoresced thin layer plates and DNA were made visible with UV light. Isolation and purification were performed as outlined in the standard protocol for isolation of DNA after polyacrylamide gel electrophoresis (see above). The quality of this procedure was routineously checked by analytical 5' phosphorylation with gamma 32 P ATP and polyacrylamide gel electrophoresis.

Preparation of the Glu-52-Aprotinin from a β-Galactosidase Lys-15-Glu-52-Aprotinin Fusion Protein Many proteins synthesized in large quantities in bacteria accumulate in an insoluble form (D. C. Williams, R. M. Van Frank, J. B. Burnett, W. L. Muth, (1982), *Science*, 215, 687). These insoluble proteins are called inclusion bodies. They may usually be solubilized only with denaturants and therefore could easily be purified from other cell proteins.

*E. coli* strain RR1 delta M15 (ATCC 35102) was transformed with plasmid pRK 48.1.1., which encodes the Glu-52-aprotinin β-Galactosidase gene downstream from an *E. coli* promotor, operator and ribosome binding site. Maximal accumulation of the 15-Glu-52-aprotinin β-Galactosidase fusion protein was 20% of total cell protein. The inclusions generally localized at the polar or sub-polar regions, with large percentage of normal-length cells having one inclusion near each pole.

Figure 8:
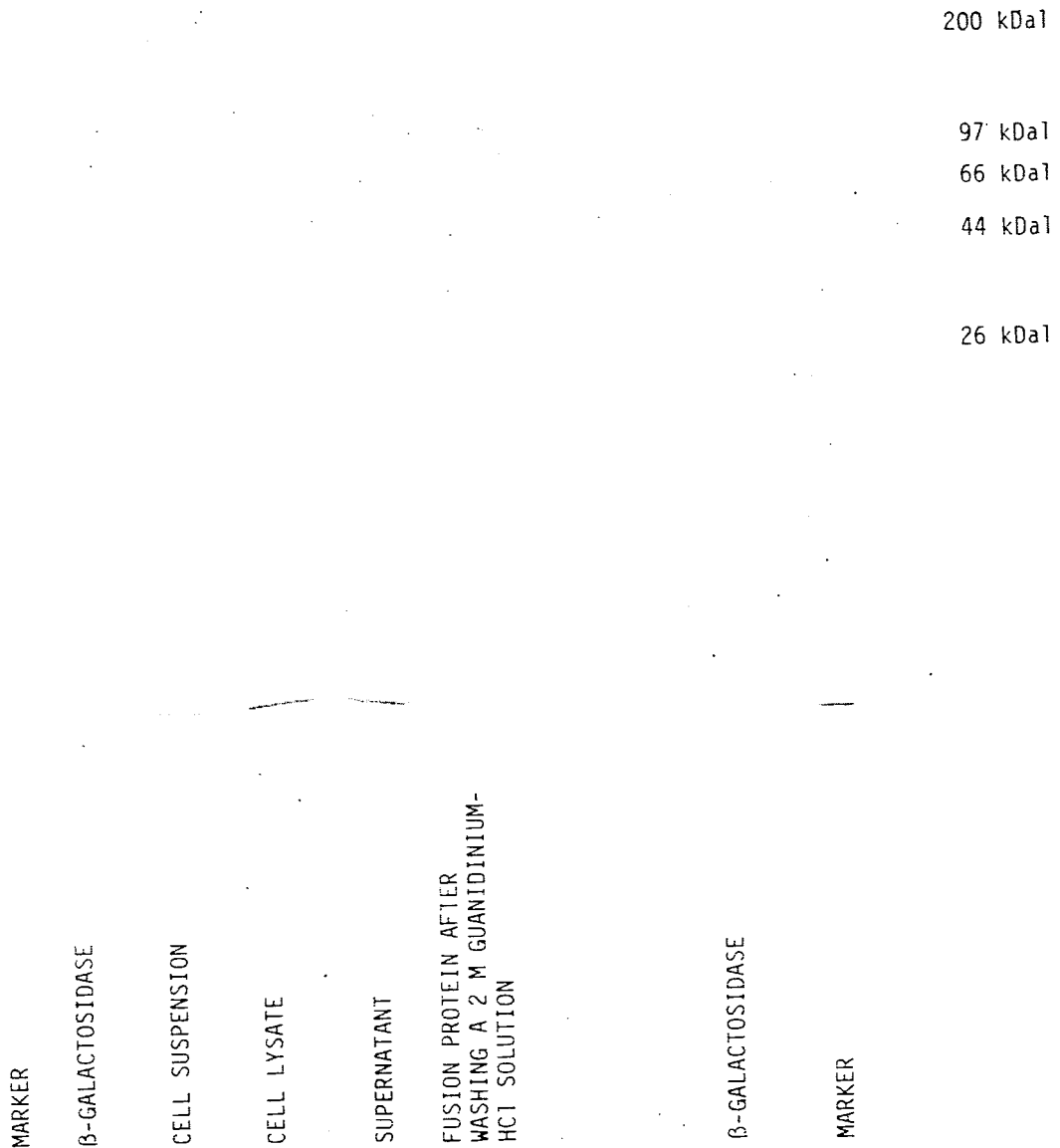
FIG. 8 shows a photograph of isolation products after gel electrophoresis.

An *E. coli* strain RR1 delta M15 overnight culture were centrifuged and the pellet was then resuspended in a breaking buffer. After sonification the cell-lysate was centrifuged for recovering the inclusion bodies. The inclusion bodies were washed with 2M guanidinium hydrochloride. The purification steps were checked by SDS-polyacrylamid electrophoreses according to Laemmli (U.K. Laemmli, (1970), *Nature* 277, 680–685), FIG. 8.

For recovering the intact Lys-15-Glu-52-aprotinin the inclusion bodies must be solubilized, cleaved by cyanogen bromide and the unfolded Glu-52-aprotinin has to be folded.

The inclusion bodies could be solubilized in 6M guanidinium hydrochloride containing a sufficient amount of DTT. After separation of nonsolubilized parts the fusion protein is precipitated by dialysing against water containing 10 mM mercaptoethanol. The wet fusion protein was dissolved in 70% formic acid and was cleaved by cyanogen bromide according to Gross et al (E. Gross, B. Witkop, (1961), *J. Amer. Chem. Soc.*, 83, 1510–1511).

Figure 10:
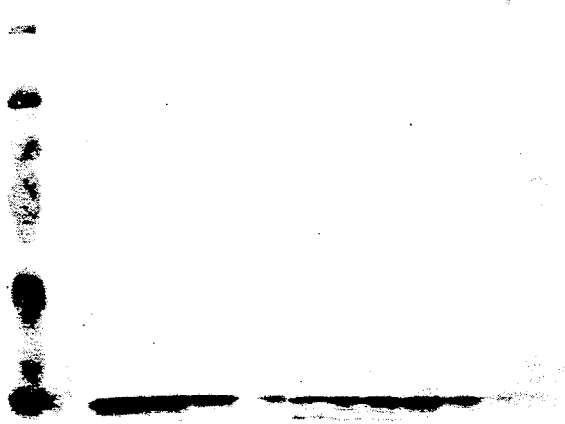
FIG. 10 is a photograph of a western blot of fractionated CNBr peptides of a Lys 15 Glu 52-aprotinin-beta-galactosidase fusion peptide.
Figure 9:
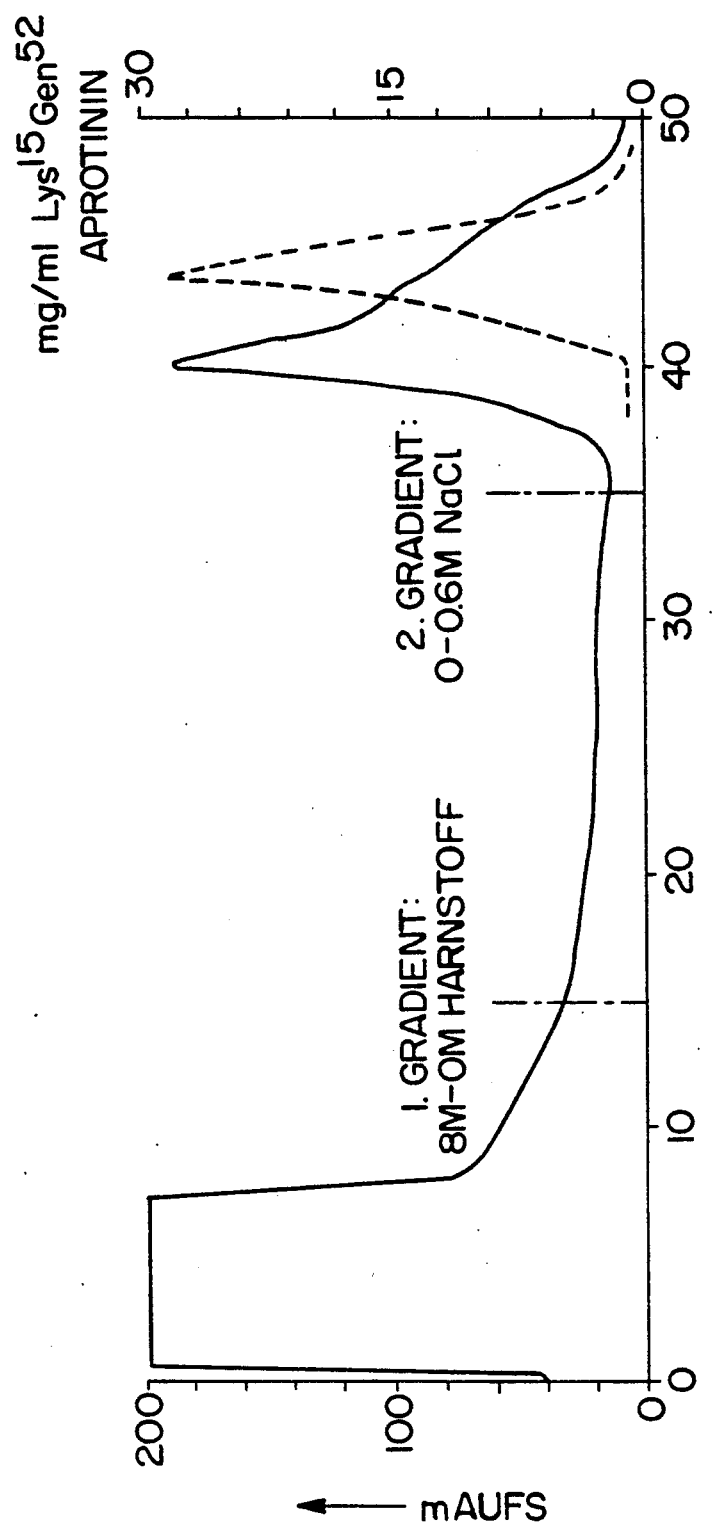
FIG. 9 is a chromatogram of a renaturated aprotinin.

The Glu-52-aprotinin was separated from the cyanogen bromide fragments of the β-Galactosidase by ion exchange chromatography and was simultaneously refolded by the procedure according to Creighton (T. E. Creighton, *Proceedings of Genex-UCLA Symposium*, (1985), Kingstones, in press) (FIG. 9). The active inhibitor could be detected by Western blot analysis (FIG. 10).

The active fractions were concentrated by evaporation and were then dialysed against 0.1M NH$_4$HCO$_3$. After lyophilization the inhibitor was purified by HPLC on a high pore RP-18 column using a gradient of 0.1% TFA in buffer A and 0.1% TFA 60% CH$_3$CN in buffer B.

The active fractions were pooled and the inhibitor was characterized by microsequencing with a gas phase sequencer according to Hewick (R. M. Hewick, M. W. Hunkapiller, L. E. Hood, W. I. Dreyer, (1981), *J. Biol. Chem.*, 256, 7990–7997). The first 20 residues from the N-terminus are identical with the expected inhibitor (Table 2). The amino acid analysis demonstrate that the inhibitor has the expected amino acid composition (Table 1).

A comparison of aprotinin and Glu-52-aprotinin by trypsin inhibitory activity shows identical dose-response curves (FIG. 11).

All these experiments show that it is possible to produce Glu-52-aprotinin as a fusion protein in *E. coli* and isolate it after cleavage and separation under renaturing conditions.

Preparation of Val-15-Glu-52-Aprotinin and Other Derivatives of Aprotinin

Figure 12:
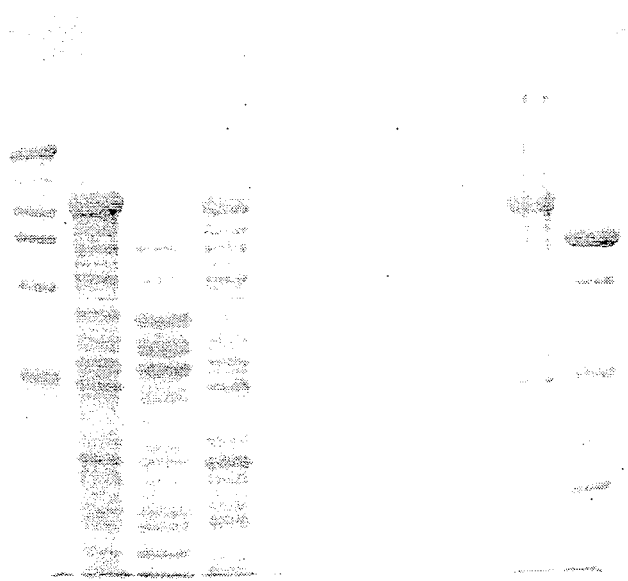
FIG. 12 is a photograph depicting the results of a 8% SDS polyacrylamide gel electrophoresis.
Figure 13:
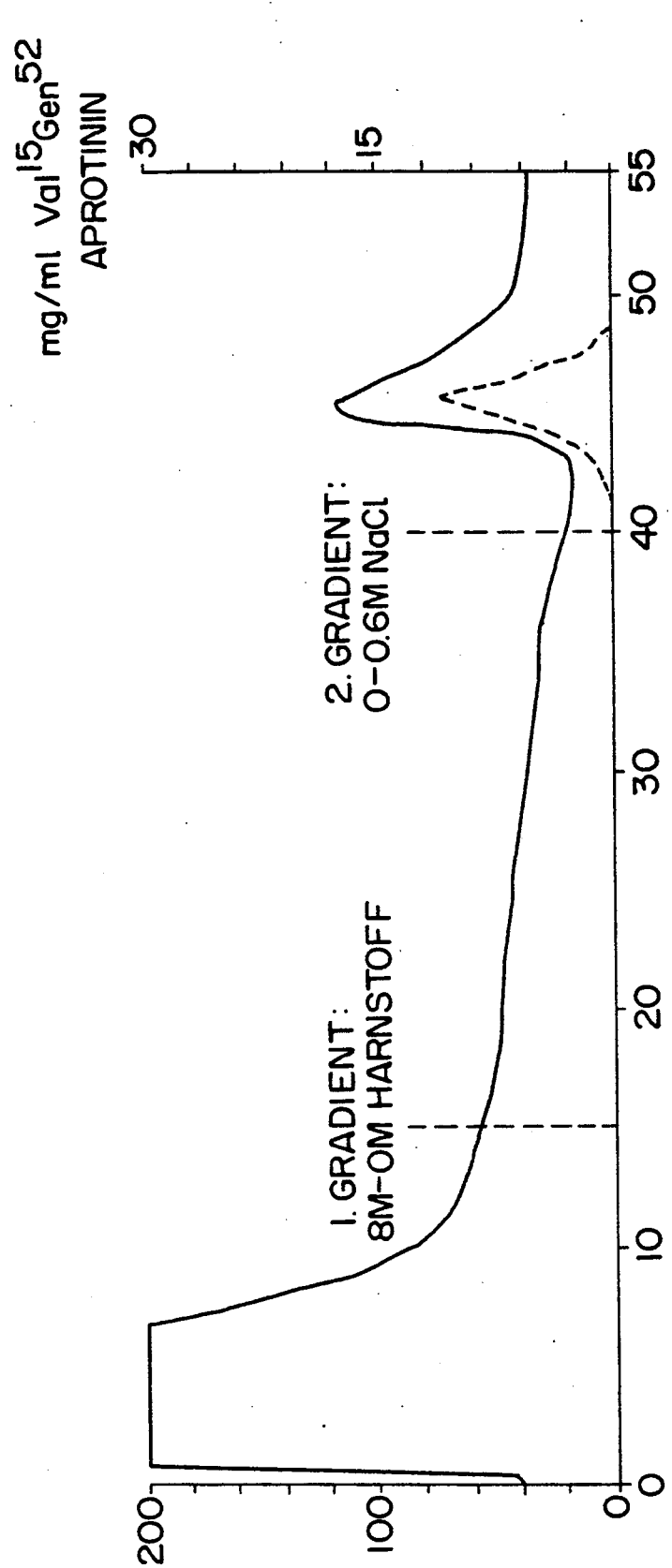
FIG. 13 is a chromatogram of renaturated of val-15 Glu-52 Aprotinin.

Val-15-Glu-52-aprotinin can be prepared in a similar way from β-Galactosidase fusion protein as described for Glu-52-aprotinin (FIG. 12, 13). The inhibitory activity was measured by an elastase inhibitory assay.

The inhibitor was characterized by amino acid analysis and N-terminal sequencing (Tables 1 and 2).

All other derivatives of aprotinin could be prepared in a similar way as described for Glu-52-aprotinin and Val-15-Glu-52-aprotinin.

TABLE 1

| Amino acid analysis of aprotinin, Glu-52-aprotinin and Val-15-Glu-52-aprotinin | | | |
|---|---|---|---|
| Amino Acid | Aprotinin | Glu-52 | Val-15-Glu-52 |
| Asp | 4,75 (5) | 4,92 (5) | 5,10 (5) |
| Thr | 2,90 (3) | 2,91 (3) | 2,85 (3) |
| Ser | 0,98 (1) | 1,01 (1) | 0,95 (1) |
| Glu | 2,90 (3) | 4,30 (4) | 4,30 (4) |
| Gly | 5,92 (6) | 5,91 (6) | 6,30 (6) |
| Ala | 6,00 (6) | 6,00 (6) | 6,00 (6) |
| Val | 1,04 (1) | 1,02 (1) | 2,06 (2) |
| Met | 0,95 (1) | — | — |
| Ile | 1,29 (2) | 1,30 (2) | 1,35 (2) |
| Leu | 2,10 (2) | 2,01 (2) | 2,01 (2) |
| Tyr | 3,92 (4) | 3,70 (4) | 3,81 (4) |
| Phe | 3,86 (4) | 4,08 (4) | 4,05 (4) |
| Lys | 3,99 (4) | 3,80 (4) | 3,10 (3) |
| Arg | 5,82 (6) | 5,75 (6) | 6,00 (6) |

The amino acids were measured after the post column derivatisation with o-phthalaldehyde. Cys and Pro were not determined.

TABLE 2

Amino acid sequencing of Glu-52 and Val-15-Glu-52-aprotinin (N-terminal)

1. Glu-52-aprotinin; about 1 nmol of the substance was sequenced over 20 cycles:

1
Arg—Pro—Asp—Phe—Cys—Leu—Glu—Pro—Pro—Tyr—

14  15                          20
Thr—Gly—Pro—Cys—Lys—Ala—Arg—Ile—Ile—Arg—

2. Val-15-Glu-52-aprotinin; about 1 nmol of the substance was sequenced over 20 cycles:

1
Arg—Pro—Aps—Phe—Cys—Leu—Glu—Pro—Pro—Tyr—

TABLE 2-continued

Amino acid sequencing of Glu-52 and Val-15-Glu-52-aprotinin (N-terminal)

|  | 14 | 15 |  |  |  |  |  | 20 |  |
|---|---|---|---|---|---|---|---|---|---|
| Thr— | Gly— | Pro— | Cys— | Val— | Ala— | Arg— | Ile— | Ile— | Arg— |

Comparison Aprotinin/Glu-52-Aprotinin

Glu-52-Aprotinin obtained after cleavage with BrCN was compared with authentic aprotinin for its inhibitory activity against porcine trypsin. Both substrates Pyrglu-Gly-Arg-pNA and Benzoyl-Arg-pNa were used for trypsin determination.

The stock solution for aprotinin was 1 μg/ml, and for Glu-52-aprotinin 0.6 μg/ml. 0-100-200-300-400-500 μl of this stock solutions were used in the test with Benzol-Arg-pNA. In the test with Pyrglu-Gly-Arg-pNA, 0-3-6-9-12-15 μl were used. Results are summarized in Table 3.

TABLE 3

|  | Aprotinin | | Glu-52-Aprotinin | |
|---|---|---|---|---|
| Substrate | Amount inhibitor per assay | ΔE/10 minutes | Amount inhibitor per assay | ΔE/10 minutes |
| Benzoyl-Arg-pNA | 0 ng | 0.91 | 0 ng | 0.91 |
|  | 100 | 0.76 | 60 | 0.77 |
|  | 200 | 0.57 | 120 | 0.68 |
|  | 300 | 0.39 | 180 | 0.58 |
|  | 400 | 0.08 | 240 | 0.44 |
|  | 500 | 0.00 | 300 | 0.30 |
| Pyr-Glu-Gly-Arg-pNA | 0 ng | 0.85 | 0 ng | 0.84 |
|  | 3 | 0.62 | 1.8 | 0.67 |
|  | 6 | 0.39 | 3.6 | 0.56 |
|  | 9 | 0.29 | 5.4 | 0.47 |
|  | 12 | 0.18 | 7.2 | 0.32 |
|  | 15 | 0.13 | 9.0 | 0.28 |

These results indicate, that aprotinin and Glu-52-aprotinin exhibit identical dose-response curves in both trypsin inhibition assays. This demonstrates not only, that the Glu-52-aprotinin contains practically 100% active molecules, but also that the equilibrium constants of the trypsin-inhibitor complexes are in the same order of magnitude.

Western Blotting

Western blotting was carried out as described by Towbin et al. (H. Towbin, T. Staehelin, I. Gordon, (1979), *Proc. Natl. Acad. Sci. USA*, 76, 4350-4354). The nitrocellulose blot was probed with rabbit polyclonal anti-aprotinin antibodies as primary and biotinylated donkey anti rabbit antibodies as secondary antibodies. Detection of immuncomplexes was performed using a streptavidin-biotinylated horseradish peroxidase complex with 4-chloro-1-naphthol as substrate as described in the supplier's manual (AMERSHAM BUCHLER GmbH, Gieselweg 1, D-3300 Braunschweig 1).

ELISA

Solid phase enzyme linked immunosorbent assay (ELISA) was performed in the competitive mode using microtiter antibodies plates as described by Müller-Esterl et al (W. Müller-Esterl, A. Oettl, E. Truscheit, H. Fritz, Fresenius Z., *Anal. Chem.*, (1984), 317, 718-719).

Amino Acid Sequence Determination

About 0.5-2 nmol of the protein were solubized in 30 μl TFA. The sample was applied to a glass fiber filter which was pretreated with 3 mg of polybrene. The sequence analysis was performed by the gas phase protein sequencer from APPLIED BIOSYSTEMS, Inc., 850 Lincoln Centre Drive, Forster City, Calif. 94404, U.S.A.) according to Hewick et al (R. M. Hewick, M. W. Hunkapiller. L. E. Hood, W. Dreger, (1981), *I. Biol. Chem.*, 256, 7990-7997). The stepwise liberated amino acid phenylthiohydantoin derivatives were analysed using a cyano-HPLC column (DU PONT, Wilmington, Del., U.S.A.) and a separation system described by Beyreuther et al (K. Beyreuther, B. Biesler, J. Bowens, R. Dildrop, K. Neufer, K. Stüber, S. Zais, R. Ehring, P. Zabel, (1983, *Modern Methods in Protein Chemistry* p. 303-325, Walter de Gruyter & Co., Berlin). A WATERS HPLC system, including a M 510 pump, a WISP 710B auto-injector, a LC-spectrophotometer M 481 and a SHIMADZU integrator C-R3A was used.

Acid Hydrolysis and Aminoacid Analysis

About 1 nmol of the protein is given in a pyrex tube to which was added 200 μl 6M HCl constant boiling HCl containing 0.05% 2-mercaptoethanol (I. T. Potts Jr., (1969), *Anal. Biochem.*, 131, 1-15). Tubes were sealed under vacuum and incubated at 110° C. for 22 h. Hydrolysates were quickly dried, redissolved in 150 μl 0.2M sodium citrate buffer pH 2.2 and filtered. Amino acid analysis were carried out with a BIOTRONIK LC 5000 amino acid analyzer equipped with a fluorescence detector and a SHIMADZU C-R2AX integrator. Amino acids were quantified after reaction with o-phthaldialdehyde essentially as described by Benson et al (J. R. Benson, P. E. Hare 1975, *Proc. Natl. Acad. Sci. USA*, 72, 619-622).

Standard Leukocyte Elastase Assay

Materials

Human leukocyte elastase was obtained from Elastin Products Company, Inc., P.O. Box 147, Pacific, Miss. 63069 U.S.A.

Methoxysuccinyl-L-alanyl-L-alanyl-L-prolyl-L-valin-p-nitroanilide—K. Nakajima, J. C. Powers, M. J. Castillo, B. M. Ashe and M. Zimmerman, *J. Biol. Chem.*, 254, 4027 (1979)—was obtained from Fa. Bachem, Feinchemikalien AG, Hauptstr. 144, CH-4416 Bubendorf/Schweiz.

Procedure

To 550 μl of a mixture of 0.2M Tris-buffer pH 8.0 containing 0.05% "TWEEN 80" and 0.05M in calcium chloride and the solution of the inhibitor 5 μl of a solution obtained on dissolution of 1 mg of the enzyme in 100 ml of 50% ethylenglykol were added. The mixture was incubated 30 min. at room temperature. Then 100 μl of a mixture of 6.5 μl of the solution of 59 mg Methoxy-succinyl-L-alanyl-L-alanyl-L-prolyl-L-valine-p-nitroanilide in 1 ml of dimethylsulfoxide and test buffer was added with stirring. The increase in optical density at 405 was recorded; %inhibition was determined by multiplying the coefficient of the increases in the optical densities of the inhibitor containing sample and the enzyme control with 100.

Inhibition of Trypsin (Assays)

Inhibition of trypsin was determined by means of either the substrate benzoyl-DL-arginine-p-nitroanilide (Merck 1670) or pyroglutamyl-glycyl-arginine-p-nitroanilide, which was synthesized from commercially available pyroglutamyl-glycine (SENN 6886) and arginine-p-nitroanilide×HBr (SENN 9123) by means of the dicyclohexyl carbodiimide condensation method. This substrate is also sold under the designation S-2444 by KABI as an urokinase substrate.

The former has the advantage of giving a linear response to the amount of Aprotinin in the sample, but has a low sensitivity. The latter one has a high sensitivity, but due to the dissociation of the aprotinin-trypsin-complex at those low concentrations, the dose-response-curve is non linear.

The buffer for the measurement of trypsin and trypsin inhibitors is 0.2M Tris, pH 8.0 containing 0.01M $CaCl_2$ and 0.05% Tween 80 ®.

The determinations can be performed in any spectral photometer which allows readings of optical densities (ODs) at 400 nm. For fully automated measurements, the photometers have to be equipped with a micro processor or must be interfaced with a suitable personal computer.

Disposable 1 cm semi micro plastic cuvettes are used for all assays. ODs are read in time intervals of 1 minute over 8 cycles at ambient temperature. The average increase of OD per minute is arbitrarily taken as the activity unit.

For inhibition assays, porcine trypsin (Merck 8350) solution (in 0.001N HCl/50% glycerol) is mixed with the inhibitor sample, adjusted to 500 μl with buffer and incubated for 10 minutes at ambient temperature. The reaction is initiated by the addition of substrate solution. More detailed information is given in the Table 4 hereinbelow. Inhibitory activities are taken from a calibration curve or automatically calculated by computer programs developed especially for this purpose.

TABLE 4

| | Assay with Pry-Glu-Gly-Arg-pNA as the substrate | Assay with Benzoyl-Arg-pNA as the substrate |
|---|---|---|
| Trypsin | 15 μl (1 μg/ml) | 20 μl (100 μl/ml) |
| Substrate: | 50 μl (0.02 M in 10% ethanol) | 50 μl (0.012 M in 10% DMSO) |

A large number of various microorganisms are known in the art as being suitable for transformation. That is, those unicellular organisms which are capable for being grown in cultures or fermentation. Preferred organisms for transformation include bacteria, yeasts and fungi.

The particular organism chosen for the work disclosed here, was E. coli RR1ΔM15, which has been deposited with the American Type Culture Collection, ATCC No. 35102. Other suitable E. coli strains may also be employed.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, caplets, pills, suppositories and ampoules, of which the content of active compound corresponds to a fraction or a multiple of an individual dose. The dosage units can contain, for example, one, two, three or four individual doses or one half, one third or one quarter of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, caplets, pills, granules, suppositories, solutions, suspensions and emulsions, pastes, ointments, gels, creams, lotions, powders and sprays may be mentioned as preferred pharmaceutical preparations.

Tablets, coated tablets, capsules, caplets, pills and granules can contain the active compound or compounds alongside the customary excipients such as (a) fillers and extenders, for example, starches, lactose, sucrose, glucose, mannitol and silica, (b) binders, for example, carboxymethylcellulose, alginates, gelatin and polyvinylpyrrolidone, (c) humectants, for example glycerol, (d) disintegrants, for example, agar-agar, calcium carbonate and sodium carbonate, (e) solution retarders, for example, paraffin and (f) absorption accelerators, for example, quaternary ammonium compounds, (g) wetting agents, for example, cetyl alcohol and glycerol monostearate, (h) adsorbents, for example, kaolin and bentonite and (i) lubricants, for example, talc, calcium and magnesium stearate and solid polyethylene glycols, or mixtures of the substances listed under (a) to (i).

The tablets, coated tablets, capsules, caplets, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used include polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example, polyethylene glycols, fats, for example, cacao fat and higher esters (for example, $C_{14}$ alcohol with $C_{16}$ fatty acid) or mixtures of these substances.

Ointments, pastes, creams and gels can contain the customary excipients in addition to the active compound or compounds, for example, animal and vegetable fats, waxes, paraffins, starch, tragacanth, cellulose derivatives, polyethylene glycols, silicones, bentonites, silica, talc and zinc oxide, or mixtures of these substances.

Powders and sprays can contain the customary excipients in addition to the active compound or compounds, for example, lactose, talc, silica, aluminium hydroxide, calcium silicate and polyamide powders, or mixtures of these substances. Sprays can additionally contain the customary propellants, for example, chlorofluorohydrocarbons.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cotton seed oil, groundnut oil, corn germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspension can contain the customary excipients in addition to the active compound or compounds, such as liquid diluents, for example water, ethyl alcohol or propylene glycol, suspending agents, for example, ethoxylated isostearyl alcohols, polyoxyethylene sorbitol and sorbitan esters, microcrystalline cellulose, aluminium metahydroxide, bentonite, agar-agar and tragacanth, or mixtures of these substances.

The formulation forms mentioned can also contain dyestuffs, preservatives and additives which improve the odour and flavour, for example, peppermint oil and eucalyptus oil, and sweeteners, for example, saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example, by mixing the active compound or compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100, mg/kg of body weight every 24 hours, optionally in the form of several individual administrations, in order to achieve the desired results. An individual administration contains the active compound or compounds according to the invention preferably in amounts of about 1 to about 250, in particular 3 to 60, mg/kg of body weight. However, it can be necessary to deviate from the dosages mentioned and, in particular, to do so as a function of the nature and body weight of the subject to be treated, the nature and severity of the illness, the nature of the preparation and of the administration of the medicine, and the time or interval over which the administration takes place.

Thus, it can suffice in some cases to manage with less than the abovementioned amount of active compound, whilst in other cases the abovementioned amount of active compound must be exceeded. The particular required optimum dosage and the type of administration of the active compounds can easily be decided by anyone skilled in the art on the basis of his expert knowledge.

E. coli transformed with expression plasmids pRK 49.2.1 and pRK 48.1.1 were deposited with Deutsche Sammlung von Mikroorganismen, Grisebachstr. 8, D-3400 Göttingen under the deposit numbers DSM 3678 and DSM 3679.

The Arg-15-homologues as for example the homologue of Example 7 are very useful in the treatment of acute inflammatory diseases as for example rheumatoid arthritis, hereditary angioneurotic edema, pneumonitis, pancreatis and shock. The Arg-15-homologues are further useful as protective agents in dialysis procedures involving artificial membranes and in extracorporal circulation.

EXAMPLES

EXAMPLE 1

Synthesis and Purification of DNA Fragments Coding for Glu-52- and Val 15-Glu-52-Aprotinin The oligonucleotides which comprise the gene were prepared using solid-phase synthetic methods. The synthetic scheme for the oligomers was as outlined and utilized proton activated, protected 2'-deoxyribonucleotide phosphoramidites. All sequential steps were performed in an automated manner on an Applied Biosystems Model 380 DNA Synthesizer using protected nucleotides, solvents, chemicals and reagents obtained from this manufacturer. The solid-phase support, also from the same manufacturer, was controlled pore glass to which the starting 3'-nucleotide was already attached. Certain modifications were introduced into the automated reaction cycle in accordance with the Manufacturer's Operating Instructions and Users' Bulletins. Upon completion of the synthesis, the oligomers were deblocked and cleaved from the solid support within the DNA synthesizer according to the manufacturer's recommendations.

Removal of the blocking groups was completed by heating the aqueous solution containing the oligomer with concentrated ammonium hydroxide at 55° C. from 4 to 24 hours in a sealed vial. The resulting solution was evaporated, the residue dissolved in 0.01M triethylammonium bicarbonate buffer, pH 7.0 (TEAB buffer). This solution was chromatographed over Sephadex-G 50 ® Gel Filtration Resin. This column was prepared in and eluted with the same TEAB buffer. Material eluting with the void volume was pooled and the solution evaporated.

A portion of the residue (10 to 40% of the absorbance units at 260 nm), dissolved in loading buffer (composition: 0.1% Bromophenol Blue, 0.1% xylene cyanol, 10 mm disodium EDTA, in formamide) was further purified by electrophoresis on polyacrylamide gels. The gel size was 18×32 cm with a thickness of 1.5 mm. The well size for each oligomer purified in this manner was 2 to 5 cm in width and up to five oligomers were purified using a single gel. The concentration of acrylamide in the gel varied from 14 to 20%, depending on the chain length of the desired product. For longer oligomers, a 14% acrylamide gel is preferred, while shorter oligomers were purified on up to a 20% acrylamide gel. The gels also contained 7M urea and Tris-borate-EDTA buffer (0.1M Tris, 0.1M Borate, 2 mM EDTA, pH 8.3). The running buffer was the same Tris-borate-EDTA mixture. Electrophoresis was carried out at 20 to 60 watts, constant power, for from 18 to 6 hours. Such standardized techniques are available in various User Information Bulletins available from Applied Biosystems.

Following completion of the electrophoresis, the gel was enclosed in plastic wrap and the oligomers visualized by shadowing with ultraviolet light. This shadowing was accomplished by placing the wrapped gel on a fluorescent thin layer chromatography plate and viewing the gel with a short wave length ultraviolet light source. The desired product appeared as the slowest migrating, major blue DNA fragment by this shadowing technique. The desired band was exised from the gel. The DNA oligomer was eluted from the gel slice onto powdered diethylaminoethyl (DEAE) cellulose using an EpiGene D-Gel ® electrophoresis apparatus. The oligomer was recovered from the cellulose by elution with 1M TEAB buffer. The buffer solution containing the oligomer was evaporated, the residue was dissolved in 0.01M TEAB buffer, and then desalted by passage over a column of Sephadex-G 50 ® as described previously. The material eluting in the void volume was pooled and lyophilized to give the final product.

Using the procedures outlined above, about 0.5 to 5.0 A260 units of each of the purified oligomers was obtained.

EXAMPLE 2

Construction of a Synthetic Aprotinin Master Genes for Glu-52- and Val-15-Glu-52-Aprotinin The construction of these specific synthetic aprotinin genes involve the assembly of 15 purified oligonucleotides (see FIG. 14). The DNA sequence shown in FIG. 3, includes the initiation codon ATG, two termination codons, TAG and TAA, the terminal restriction sites Eco RI, Hind III and Bam HI and internal restriction sites. The choice of these sites facilitated the cloning of the coding sequence and its modification.

The construction used to generate this synthetic gene employed besides the fragments the use of Polynucleotid Kinase, T4 DNA ligase and restriction enzymes as described in detail within material and methods.

Fifteen purified oligonucleotide fragments were dissolved in 50 mM TEABC (triethylammonium bicarbonate buffer, pH 7.5), final concentration 10 pmol/μl. The phosphorylation of all fragments was done in 4 separate parts (Frag. 1,3; Frag. 2,4,6; Frag. 5,7,9,11,13; Frag. 8,10,12,14,16). For preparative purposes, 80 pmol of each fragment, respectively, were dissolved in a mixture of 1X PNK-Mix, 2 μM ATP, 0.5 uCi 32 P gamma ATP per 10 pmol fragment, 10 units PNK per pmol fragment, so that the total volumes were for Frag. 1,3; 300 μl, for Frag. 2,4,6; 400 μl, for Frag. 5,7,9,11,12; and Frag. 8,10,12,14,16; 700 μl. Reaction for each part was carried out at 37° C. for 30 minutes. All parts were phenolized, ethanol precipitated, washed and dried.

For hybridization purposes, Frag. 1,3 and Frag. 2,4,6 (block A) were dissolved and mixed in 1X Ligase-Mix; total volume 120 μl, incubated for 5 minutes at 70° C. and cooled down to room temperature within 5 hours. The other fragments (block B) were hybridized in 240 μl according to the same procedure.

For ligation purpose, block A solution was supplemented with 12 μl 10 mM ATP, 12 μl 100 mM DTE, 20 μl T4 DNA ligase and block B solution with twice as much. Reaction was carried out at 14° C. for 7 hours. After this 10 μl T4 DNA ligase was added for block A and 20 μl for block B and again incubated at 14° C. for 45 minutes. The mixtures were phenolized, ethanol precipitated and dried.

The obtained block A was dissolved in 90 μl 1X SP-100 and 10 μl Eco RI (10 μ/μl), block B in 90 μl 1X SP-50 and 10 μl Bam HI and incubated at 37° C. for 1 hour. The reactions were stopped by phenol extraction and ethanol precipitation, 6% polyacrylamide gel electrophoresis was carried out, and the DNA blocks were recovered according to the same procedure as described above.

Equal amounts of radioactive labelled block A and B were dissolved in water, adjusted to 1X ligase mix and hybridized as described above for final ligation to a synthetic gene. Therefor, 3 μl 10 mM ATP, 3 μl 100 mM DTE, 3 μl T4 DNA ligase were added to 22 μl of a hydridization mixture and incubated at 14° C. for 7 hours. Again 1 μl T4 DNA ligase was added and this reaction was carried out at 14° C. for 45 minutes. The ligation product was purified by phenol extraction and ethanol precipitation. A standard restriction enzyme digestion (Bam HI 1.5 μl, Eco RI 1.5 μl double digestion) in SP-50 was performed. The material was phenol extracted and before ethanol precipitation the aqueous solution was adjusted to 3 mM MgCl$_2$ 0.3M sodium acetate. Then, 6% polyacrylamide gel electrophoresis was carried out, and the gene was recovered according to the same procedure as described above.

EXAMPLE 3

Construction of Recombinant Plasmids pRK 63.1.1 and pRK 54.1.1

The plasmid chosen for experimental aprotinin cloning was pUC 8 (J. Vieira and J. Messing, (1982), *Gene*, 19, 259). This cloning vector consists of a pBR 322 derived ampicillinase gene and the origin of DNA replication ligated to a portion of the lac Z gene which contains an array of unique restriction enzyme recognition sites. When this vector is introduced into lac E. coli, the transformant give rise to blue colonies on appropriate indicator plates. Cloning DNA fragments into any of the multiple restriction sites, for example between Eco RI and Bam HI, inactivates the lac gene giving rise to white colonies.

Vector Preparation

For ligating the synthetic aprotinin master gene into pUC 8, a preparative vector preparation was performed. Purified pUC 8 DNA (about 30 pmol) were digested twice with Eco RI and Bam HI under standard restriction endonuclease digestion conditions, to cut out a small internal Eco RI-Bam HI fragment. This preparation was dephosphorylated with calf intestine phosphatase as described above, separated by agarose gel electrophoresis and the large Eco RI-Bam HI fragment of the vector was purified (standard conditions). This procedure facilitates enormously the further work with the vector, because self ligation of vector molecules at the Eco RI and Bam HI termini are excluded and the background of transformants is reduced drastically.

Ligation

Figure 4:
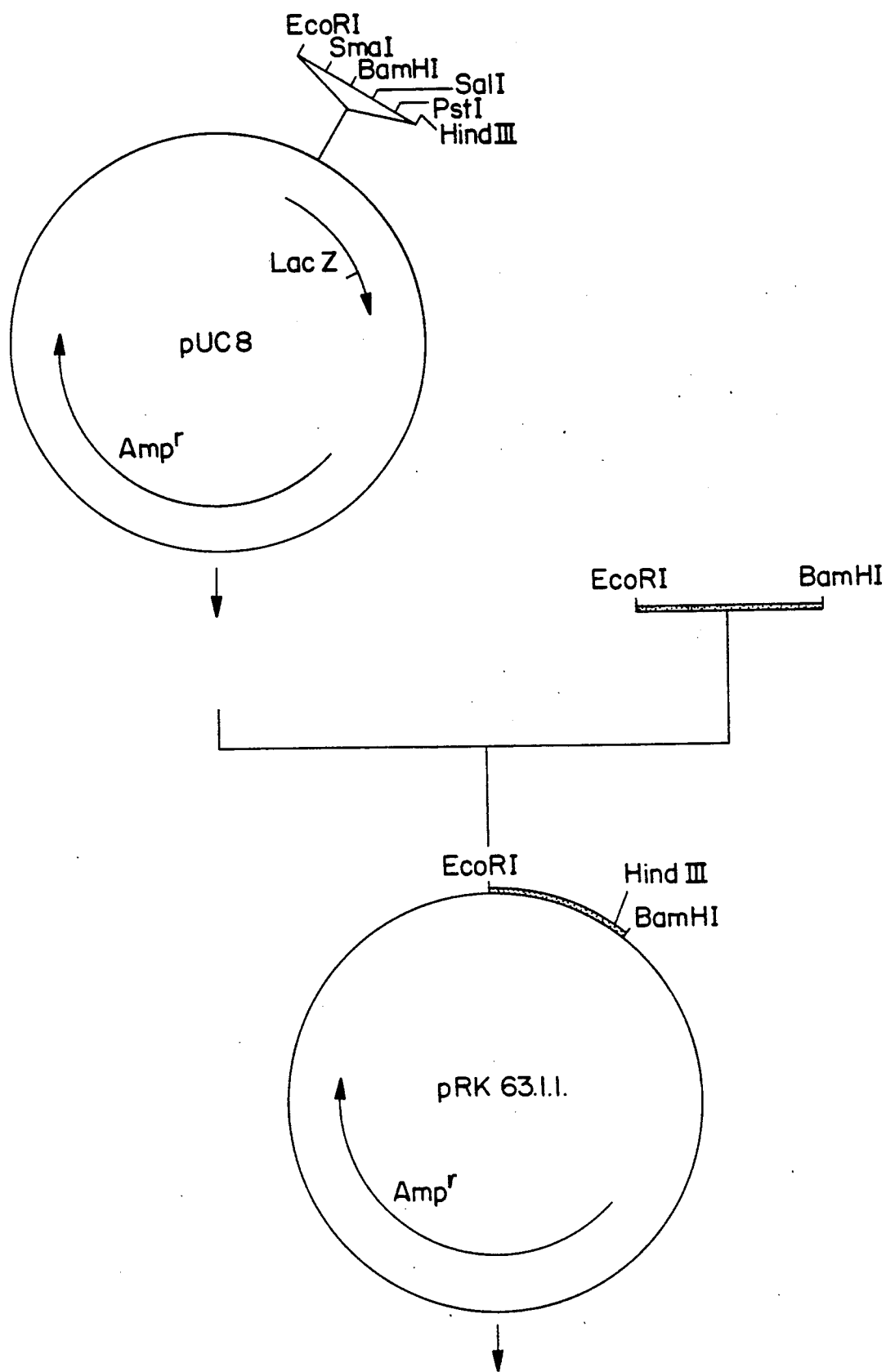
FIG. 4 schematically depicts the construction of a plasmid according to the present invention.
Figure 5:
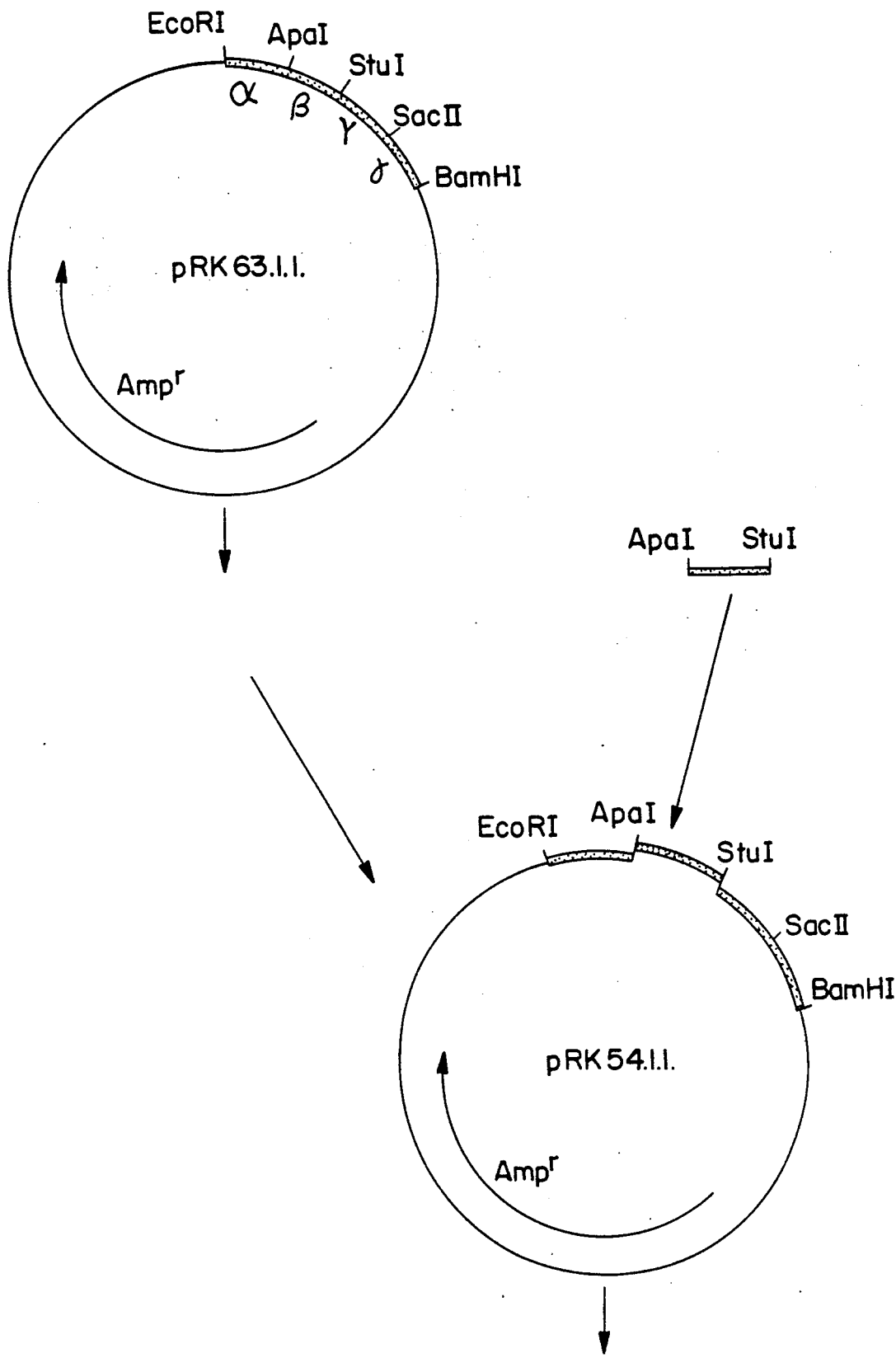
FIG. 5 schematically depicts the construction of a plasmid according to the present invention.

The construction of pRK 63 (see FIG. 4) was done by ligating the total amount of purified synthetic aprotinin gene with 1 pmol vector (1.8 units T4-DNA-ligase, 1X ligase mix, total volume 45 μl, incubation at 14° C. for 7 hours, addition of 1 unit T4-DNA-ligase and reincubation at 14° C. for 45 minutes).

Transformation

Using the transformation procedure from D. Hanahan, supra (for details see the standard transformation procedure) *E. coli* strain RRI delta M15 (A. Kalnins et al, (1983), *EMBO Journal* 2, 593; ATCC 35102) was used as receptor cell. 15 "white" transformants were received after transformation with 50% of the ligation material on indicator plates containing 200 μg/ml ampicillin. All 15 transformants were screened using a modification of the rapid analytical plasmid isolation method of Birnboim and Doly (1979) (see above). Therefore, pellets of the 15 samples were redissolved in 30 μl 1X SP-100 containing 1 μg RNase A. A restriction digestion with Eco RI and Bam HI was performed.

After gel electrophoresis four of the fifteen transformants were found to contain plasmid DNA carrying an Eco RI-Bam HI fragment approximately 200 base pairs long.

All transformants which carried this Eco RI-Bam HI fragment were grown in large scale and plasmids from each were isolated and analysed further. Two of them were sequenced according to the procedure of Maxam and Gilber (Proc. Natl. Acad. Sci. U.S.A. (1977) 74, 560–564) all showed the correct sequence, demonstrating the excellence of chemical synthesis and construction.

Plasmid pRK 54.1.1 (Val-15-Glu-52 aprotinin) was constructed by a simple exchange of the beta block of the synthetic gene, which is an Apa I-Stu I fragment, with a beta block containing a codon for Val at position 15 instead of Lys.

About 100 pmol of the synthetic ss DNA fragments BEA 4A and BEA 4B (see FIG. 2B) were dissolved in 20 μl water, heated for 5 minutes at 95° C. and cooled down slowly to room temperature (5 hours). The hybridized unphosphorylated fragment was ligated with 1.5 pmol purified DNA from pRK 63.1.1. missing the Apa I-Stu I fragment. Standard ligation was done 30 μl ligation mix. Transformation of *E. coli* RRIΔM15 was done with 50% of the ligation mixture. From 1500 transformants 24 were tested by an analytical plasmid isolation and restriction analysis. All were positive and two of them were sequenced by the M 13 Dideoxynucleotide Sequencing System from BioLabs, Beverly, Mass., U.S.A. The transformant pRK 54.1.1 were used for further experiments.

EXAMPLE 4

Construction of Expression Plasmids pRK 48.1.1 and pRK 49.2.1

For expression of aprotinin as a fusion protein a plasmid was constructed in which the aprotinin gene was located at the carboxy terminus of the β-galactosidase gene as it was shown in similar experiments by U. Rüther and B. Müller-Hill, (1983), *EMBO Journal,* 2, 1791–1794 and in German Pat. appl. DE-OS No. 33 09 501.9.

For cloning the synthetic aprotinin gene in expression vector pUR 278 cloning sites Bam HI and Hind III were chosen. Therefor, it was necessary to modify the aprotinin gene by adding a Bam HI site at the 5' Eco RI end of the gene and using the Hind III site at the 3' end (see also FIG. 6).

50 pmol pRK 63.1.1 DNA were completely digested overnight at 37° C. with Eco RI (15 pmol hit/μl) in 120 μl 1X SP-100. The protruding 5' Eco RI ends of this DNA material were filled by an enzymatic reaction with DNA polymerase I (Klenow fragment), dATP and dTTP (Maniatis et al, (1982), supra) 600 pmol of dried alpha 32 P ATP (250 uCi) were solved and mixed with 160 μl DNA (50 pmol), 10 μl 1 mM dATP (10 000 pmol), 20 μl NT buffer. Than 10 μl DNA polymerase I (Klenow, (50μ) were added and a first incubation at room temperature took place. After 30 minutes, 10 μl 1 mM dTTP (10 000 pmol) were added together with 5 μl polymerase (25μ) and the second incubation at room temperature took place. The material was phenol/sevag extracted, molecular weight fractions radioactive labelled, were pooled, ethanol precipitated, washed, solved in 50 μl TE and stored at 20° C.

20 μl of this material with flush ends were used for ligation with Bam HI linker. Therefore, 400 pmol of 5' Bam HI linker labelled with gamma 32 P ATP (standard 5' phosphorylation procedure) were ligated to 40 pmol DNA ends (standard ligation conditions, 4.5μ T4 DNA ligase, total volume 60 μl). To control the quality of linker ligation an analytical gel electrophoresis were performed. Complete ligation was achieved after adding 100 pmol Bam HI linker, 1.8 units T4 DNA ligase, incubation at 20° C. for 1 hour and adding 1 unit T4 DNA ligase and incubation at 14° C. for 18 hours. The reaction mixture was phenol/sevag extracted, ethanol precipitated, washed, dried and solved in 40 μl TE.

For preparation of the synthetic aprotinin gene with Bam HI and Hind III termini, the linkered linear plasmid (10 pmol) was cut first with Hind III (10.5 pmol hit/μl, 5 hours, 37° C.), and then with Bam HI (40 pmol hit/μl, 20 hours, 37° C. standard conditions). The fragment was isolated after separation on 6% polyacrylamide gel electrophoresis and carefully purified (see standard procedure).

Vector Preparation

The parental vector pUR 278 (about 5 pmol) was cut first with Hind III (standard conditions) purified by phenol/sevag extraction, ethanol precipitation, redissolved and then digested with Bam HI (standard conditions). This material was loaded on a 1% agarose gel, electrophorized, isolated and purified according to the standard conditions, to get rid of the 18 base pair long Bam HI-Hind III fragment which would compete in ligation with the synthetic aprotinin gene.

Ligation and Tranformation

For ligation, a 0.3 pmol vector, 1.5 pmol fragment (approximately), 2 units T4 DNA ligase were used (standard conditions: total volume 30 μl, incubation: 4 hours at 14° C.).

Transformation was performed with *E. coli* strain RR1 delta M 15 as host using one third of the ligation mixture (standard conditions). A total of 173 "blue" colonies were received on indicator plates containing 200 μg ampicillin/ml. From this 12 transformants were analysed further by rapid analytical plasmid isolation (standard conditions). Of 173 transformants 30 should be background transformants, calculated on the percentage of transformants received by religation of vector. This result was confirmed by restriction analysis of plasmids of the 12 transformants. 8 of them were positive showing a Bam HI-Hind III restriction fragment of about 200 base pairs. Positive recombinant plasmids were also linearized by Sst II and unique restriction site within the aprotinin gene. Base sequence analysis according to Maxam and Gilbert, 1980, revealed that the plasmid pRK 48.1.1 has inserted the desired aprotinin DNA fragment (see FIG. 6). Plasmid pRK 48.1.1 was used for further analysis and expression work.

The construction of plasmid pRK 49.2.1 was done by exact the same procedure using the Val-15-Glu-52 gene from pRK 54.1.1. The positive recombinant plasmid 49.2.1 showed the correct DNA sequence and this construction was used for further analysis and expression work.

Detection of Expression of
β-Galactosidase-Glu-52-Aprotinin and
β-Galactosidase-Val-15-Glu-52-Aprotinin To attempt expression of each of these constructions, E. coli strains with pRK 48.1.1 (deposited at DSM, DSM No. 3679) and pRK 49.2.1 (deposited at DSM, DSM No. 3678) were inoculated into 2 ml LB-ampicillin medium supplemented with 4 μl of 0.1M IPTG. A clone containing pUR 278 without aprotinin gene insert was also inoculated into culture medium to provide for the a negative control for the assays. After 12–16 hours growth at 37° C. with agitation samples of 1 ml were used directly for inoculation of 100 ml LB-ampicillin medium. After growing for 12–16 hours at 37° C. with agitation, the cells were harvested by centrifugation at 5000 rpm for 10 minutes in a Beckmann JA 10 rotor.

Direct detection of fusion proteins were performed with SDS Polyacrylamide gel electrophoresis according to Laemmli, U.K., (1970), *Nature*, 277, p. 680, see also B. D. Hames and D. Rickwood, (1981), *Gel Electrophoresis of Proteins*, IRL Press Limited, Oxford, England).

Figure 7:
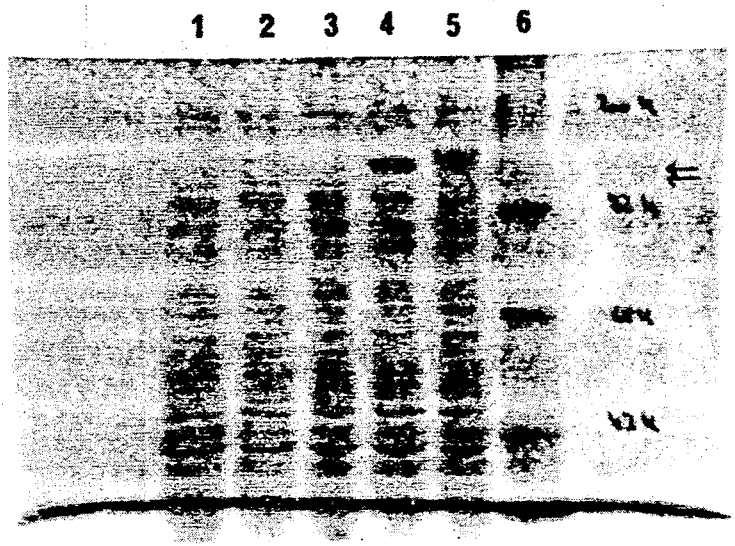
FIG. 7 shows a photograph of a 7.5% SDS-Polyacrylamide-Gel after electrophoresis and staining.

Per lane about 1×10E9 cells were centrifuged and redissolved in a 1:5 dilution of SDS sample buffer (0.3M Tris HCL pH 8.8, 50% glycerol, 5% SDS, 25% mercapto ethanol). After electrophoresis gels were stained with Coomassie blue. FIG. 7 shows a typical pattern of E. coli proteins with the inducible β-galactosidase Glu-52 aprotinin fusion protein.

Solutions

Breaking buffer:
50 mM Tris
100 mM Sodium chloride;
10 mM Magnesium chloride;
10 mM Mercaptoethanol;

2M Guanidinium-HCl-solution:
2M Guanidinium-HCl;
50 mM Tris-HCl, pH 7.7
100 mM Sodium chloride;
10 mM Mercaptoethanol;

6M Guanidinium-HCl-solution:
6M Guanidinium-HCl;
50 mM Tris-HCl;
100 mM Sodiumchloride;
10 mM Mercaptoethanol.

EXAMPLE 5

Preparation of Glu-52-Aprotinin

1. Isolation and Cyanogen Bromide Cleavage of β-Gal-Fusion Protein Lys-15-Glu-52-Aprotinin For preparation purposes, 6 liters of an E. coli overnight culture strain RR1 delta M15 were centrifuged for 15 minutes at 8000 rpm. The cell pellet, about 15 g in weight, was resuspended in 30 ml of breaking puffer and sonified for 6 minutes (ice cooling). The cell lysate was centrifuged for 20 minutes at 20000 rpm. The supernatant was discarded. The pellet, about 10 g was resuspended in 20 ml of 2M guanidinium hydrochloride solution and was homogenized. After centrifugation for 20 minutes at 2000 rpm, the supernatant was discarded.

The pellet, about 8 g, was dissolved under a N₂ atmosphere in 20 ml 6M guanidinium hydrochloride solution containing 200 mg Dithiothocitol and reduced for 1 hour at 50° C. The solution was centrifuged for 10 minutes at 10000 rpm and dialysed for 24 hours against water containing 10 mM mercaptoethanol. The precipitated fusionprotein was collected by centrifugation for 20 minutes at 20000 rpm. The wet fusion protein was dissolved in 30 ml conc. formic acid and then diluted to 70% with water. The fusion protein was cleaved by adding 4 g of cyanogen bromide and incubation for 18 hours under nitrogen atmosphere in the darkness. The reaction was stopped by diluting with 200 ml water. The water and the volatile by-products were removed by freeze drying. The cyanogen bromide cleavage was checked by SDS gel electrophoresis according to Laemmli, supra. The yield was about 1.5 g of cyanogen bromide fragments. In a series of experiments the yields varied from 0.8 to 2.5 g.

Solutions

Buffer A, pH 8.2
50 mmol Tris-HCl
1 mmol EDTA
Adjust to pH 8.2

Buffer B, pH 8.2
8M Urea
1 mmol Bis-(2-hydroxyethyl)-disulfide
1 mmol 2-Mercaptoethanol
in Buffer A;

Buffer C, pH 8.2
1 mmol Bis-(2-hydroxyethyl)-disulfide
1 mmol 2-Mercaptoethanol
in Buffer A;

Buffer D, ph 8.2
0.6 mol Sodium chloride in Buffer A.

2. Separation and Renaturation of Glu-52-Aprotinin

About 300 mg of freeze dried Lys-15-Glu-52-aprotinin β-galactosidase cyanogenbromide fragments were dissolved in 300 ml buffer B containing 300 mg DTT. The solution was reduced for 1 hour at 50° C. under a nitrogen atmosphere. Then the solution was applied to a CM-Sephadex column (25×100 mm) filled with about 15 ml CM-sepharose Fast Flow ®. The column was equilibrated with buffer B. The column was washed with buffer B until the baseline was stable. In a first linear gradient elution the column was developed with 100 ml of buffer B and 100 ml of buffer C. Before the second linear elution gradient was applied the column was washed with buffer A until the baseline was stable. The second gradient was formed with 100 ml buffer A and 100 ml buffer D. The peak fractions were tested for trypsin inhibitory activity and by ELISA and Western Blot (FIG. 10). In a series of experiments the yield estimated by the different tests was in the range of 0.4–2 mg.

3. Purification of Glu-52-Aprotinin by Reversed Phase HPLC

The active fractions were concentrated by evaporation and then dialysed against 0.1M NH₄HCO₃ pH=7.5 for 18 hours. After lyophilization the inhibitor was dissolved in 0.1% TFA and fractionated by reversed phase chromatography on high pore RP-18 column (BIORAD) using a gradient of 0.1% TFA in buffer A and 0.1% Trifluoro acetic acid 60% in buffer B. The inhibitor was characterized by N-terminal sequencing and amino acid analysis.

EXAMPLE 6

Expression of Val-15-Glu-52-Aprotinin and Characterisation of the Product

The fermentation of *E. coli* transformant with plasmid pRK 49.2.1 and the purification of the Val-15-Glu-52-aprotinin was performed according to the same procedures described in Example 5, with the difference that the activity was tested by an elastase inhibitory assay instead of the trypsin inhibitory test. The Val-15-Glu-52-aprotinin elutes earlier from the CM Sephadex column than the Glu-52-aprotinin.

In a series of experiments the yield estimated by the different tests was 0.1–1 mg.

The same HPLC purification was applied for the isolation of Val-15-Glu-52-aprotinin. The inhibitory activity was determined by assaying leucocyte elastase inhibition. The inhibitor was characterized by N-terminal sequencing and amino acid analysis.

EXAMPLE 7

Construction, Expression and Characterization of Arg-15-Glu-52-Aprotinin

For construction of a Arg-15-Glu-52-aprotinin gene, the beta block was exchanged (FIG. 1), which is the Apa I-Stu I DNA fragment, of the Val-15-Glu-52-aprotinin gene, cloned in plasmid pRK 54.1.1.

This fragment was replaced by a corresponding fragment which codes at amino acid position 15 for Arginine by codon CGT. The resulting recombinant vector was named pNH 01.1.1, partially sequenced and used for further experiments.

At the 5' end of the Arg-15-Glu-52-aprotinin gene a Bam HI site was added and the isolated gene was ligated into the Bam HI-Hind III cleaved expression vector pUR 278.

This DNA was used for transformation of *E. coli* RR1 delta M15 and a transformant containing the new expression plasmid pRK 112.1.1 was selected.

From this transformant a β-galactosidase Arg-15-Glu-52-aprotinin fusion protein was isolated and Arg-15-Glu-52-aprotinin was purified after cyanogen bromide cleavage as described earlier.

Surprisingly, kinetic studies showed that the recombinant Arg-15-Glu-52-aprotinin is a very potent inhibitor of human plasma kallikrein ($K_i = 3.2 \times 10^{-10}(M)$) cationic and anionic human Trypsin with $K_i$-values below $10^{-11}(M)$. The $K_i$ values were determined by the method of M. W. Empie and M. Laskowski, Jr., *Biochem.* 21, 2274 (1982).

It will be appreciated that the instant specification and claims are set forth by way of illustration and not limitation, and that various modifications and changes may be made without departing from the spirit and scope of the present invention.

What is claimed is:

1. A pharmaceutical composition containing a microbially produced aprotinin homolog which is substituted in position 52 by an amino acid selected from the group consisting of Glu, Leu, Val, Thr and Ser and containing a pharmaceutically acceptable carrier.

2. A method of treating a patient suffering from an excessive release of pancreatic elastase, serum elastase or leukocyte elastase comprising administering to said patient a therapeutically effective amount of a microbially produced aprotinin or aprotinin homolog according to claim 1.

3. A pharmaceutical composition according to claim 1 containing a microbially produced aprotinin homolog substituted in position 15 by a naturally occuring amino acid.

4. A pharmaceutical composition containing a microbially produced aprotinin homolog which is substituted in position 52 by any naturally occurring amino acid except methionine and containing a pharmaceutically acceptable carrier.

5. A pharmaceutical composition according to claim 3 wherein said amino acid is selected from the group consisting of Arg-15, Val-15, Ile-15, Leu-15, Phe-15, Gly-15, Ser-15, Trp-15, Tyr-15 and Ala-15.

6. A pharmaceutical composition according to claim 1 wherein the amino acid in position 52 is Glu.

7. A pharmaceutical composition according to claim 1 wherein the amino acid in position 15 is Val or Arg and the amino acid in position 52 is Glu.

8. A pharmaceutical composition according to claim 1 wherein the amino acid at position 15 is Ile and the amino acid at position 52 is Glu.

9. A pharmaceutical composition according to claim 1 wherein the amino acid at position 15 is Leu and the amino acid at position 52 is Glu.

* * * * *

UNITED STATES PATENT AND TRADEMARK OFFICE
CERTIFICATE OF CORRECTION

PATENT NO. : 5,032,573

DATED : July 16, 1991

INVENTOR(S) : Auerswald et al.

It is certified that error appears in the above-identified patent and that said Letters Patent is hereby corrected as shown below:

Title Page     Insert -- [30] Foreign Application Priority Data:
                    Mar. 26, 1986 Great Britain........8607523 --

Signed and Sealed this

Twenty-third Day of March, 1993

*Attest:*

STEPHEN G. KUNIN

*Attesting Officer*     *Acting Commissioner of Patents and Trademarks*